US008901175B2

(12) United States Patent
Miltner et al.

(10) Patent No.: US 8,901,175 B2
(45) Date of Patent: Dec. 2, 2014

(54) USE OF OPIOIDS OR OPIOID MIMETICS FOR THE TREATMENT OF RESISTANT CANCER PATIENTS

(75) Inventors: Erich Miltner, Ulm (DE); Claudia Friesen, Ulm (DE); Andreas Alt, Vöhringen (DE)

(73) Assignee: Universität Ulm, Ulm (DE)

( * ) Notice: Subject to any disclaimer, the term of this patent is extended or adjusted under 35 U.S.C. 154(b) by 499 days.

(21) Appl. No.: 13/056,918

(22) PCT Filed: Jan. 29, 2009

(86) PCT No.: PCT/EP2009/000584
§ 371 (c)(1),
(2), (4) Date: Apr. 28, 2011

(87) PCT Pub. No.: WO2010/012319
PCT Pub. Date: Feb. 4, 2010

(65) Prior Publication Data
US 2011/0270011 A1 Nov. 3, 2011

(30) Foreign Application Priority Data

Jul. 31, 2008 (EP) .................................... 08013741

(51) Int. Cl.
*A01N 33/02* (2006.01)
*A61K 31/135* (2006.01)
*A01N 43/42* (2006.01)
*A61K 31/44* (2006.01)
*C07D 211/56* (2006.01)
*C07D 211/92* (2006.01)
*C07D 471/00* (2006.01)
*C07D 489/12* (2006.01)
*C07D 491/00* (2006.01)
*C07D 498/00* (2006.01)
*C07D 513/00* (2006.01)
*C07D 515/00* (2006.01)
*A61K 31/137* (2006.01)
*A61K 31/485* (2006.01)
*A61K 33/24* (2006.01)
*A61K 45/06* (2006.01)
*A61K 31/475* (2006.01)
*A61K 31/704* (2006.01)
*A61K 41/00* (2006.01)
*A61K 31/519* (2006.01)
*A61K 31/7068* (2006.01)

(52) U.S. Cl.
CPC ............. *A61K 31/485* (2013.01); *A61K 31/137* (2013.01); *A61K 33/24* (2013.01); *A61K 45/06* (2013.01); *A61K 31/475* (2013.01); *A61K 31/704* (2013.01); *A61K 41/00* (2013.01); *A61K 31/519* (2013.01); *A61K 31/7068* (2013.01)

USPC ............ 514/648; 514/282; 546/224; 546/39; 546/44

(58) Field of Classification Search
USPC ...................... 514/648, 282; 546/224, 39, 44
See application file for complete search history.

(56) References Cited

FOREIGN PATENT DOCUMENTS

WO    WO2006/124413    11/2006

OTHER PUBLICATIONS

Maneckjee et al. Proc. Natl. Acad. Sci., 1992, vol. 89, pp. 1169-1173.*
Lowe et al. Carcinogenesis, 2000, vol. 21, No. 3, pp. 485-495.*
Yoshida, Akira et al., "Opiod analgesic-induced apoptosis . . . ", Intern. Journal of Molecular Medicine, vol. 6, No. 3, Sep. 2000, p. 329-335.
Kugawqa, Fumihiko et al., "Apoptosis of NG108-15 cells . . . ", Biological and Pharmaceutical Bulletin, vol. 23, No. 8, Aug. 2000.
Notas et al., "The inhibitory effect of opioids on HepG2 cells . . . ", European Journal of Pharmacology, Eslevier BV, NL, vol. 555, No. 1, 2005, p. 1-7.
Lovekamp et al., "Inhibition of human multidrug resistance . . . "Brain Research, Elsevier, Amsterdam, NL, vol. 902, No. 1, 2001, p. 131-134.
Hassam Hazem et al., "Oxydone induces overexpression . . . ", Journal of Pharmaceutical Science, American Pharmaceutical Association, vol. 96, No. 9, 2007, p. 2492-2506.
He, J. et al., "Role of mitochondrial cytochrome c in . . . ", The Journal of Pharmacology and Experimental Therapeutics, Dec. 2000, p. 896-903.
Dey et al. "Cocaine exposure in vitro induces apoptosis . . . ", Neuroscience, New York, vol. 144, No. 2, 2006, p. 509-21.
Li et al., "Cocaine induced apoptosis in rat testes . . . ", Journal of Urology, Lippincott Williams & Wilkings, US, vol. 162, No. 1, 1999, p. 213-216.
Li, Guohu et al., "Cocaine induces apoptosis in fetal rat . . . ", The Journal of Pharmacology and Experimental Therapeutics, Jan. 2005, p. 112-119.
Cunha-Oliveira, T. et al., "Mitlochondrial dysfunction and caspase activation . . . ", Brain Research, Elsevier, NL, vol. 1089, No. 1, May 2006, p. 44-54.
Bergmann, JP, Harris D. Radioresistance, chemoresistance and apoptosis resistance. Radiation Oncology 1997, No. 27, p. 47-57.
Carbonari, M., et al. "Detection and characterization of apoptotic peripheral blood lymphocytes in human immunodeficiency . . . ", Blood 1994, No. 83, 1268-77.

(Continued)

*Primary Examiner* — Samira Jean-Louis
(74) *Attorney, Agent, or Firm* — Henry M. Feiereisen LLC; Ursula B. Day

(57) ABSTRACT

The use of opioids or opioid mimetics is suggested for the manufacture of a medicament for the treatment of resistant cancer patients.

10 Claims, 17 Drawing Sheets

(56) References Cited

OTHER PUBLICATIONS

Figure 1:
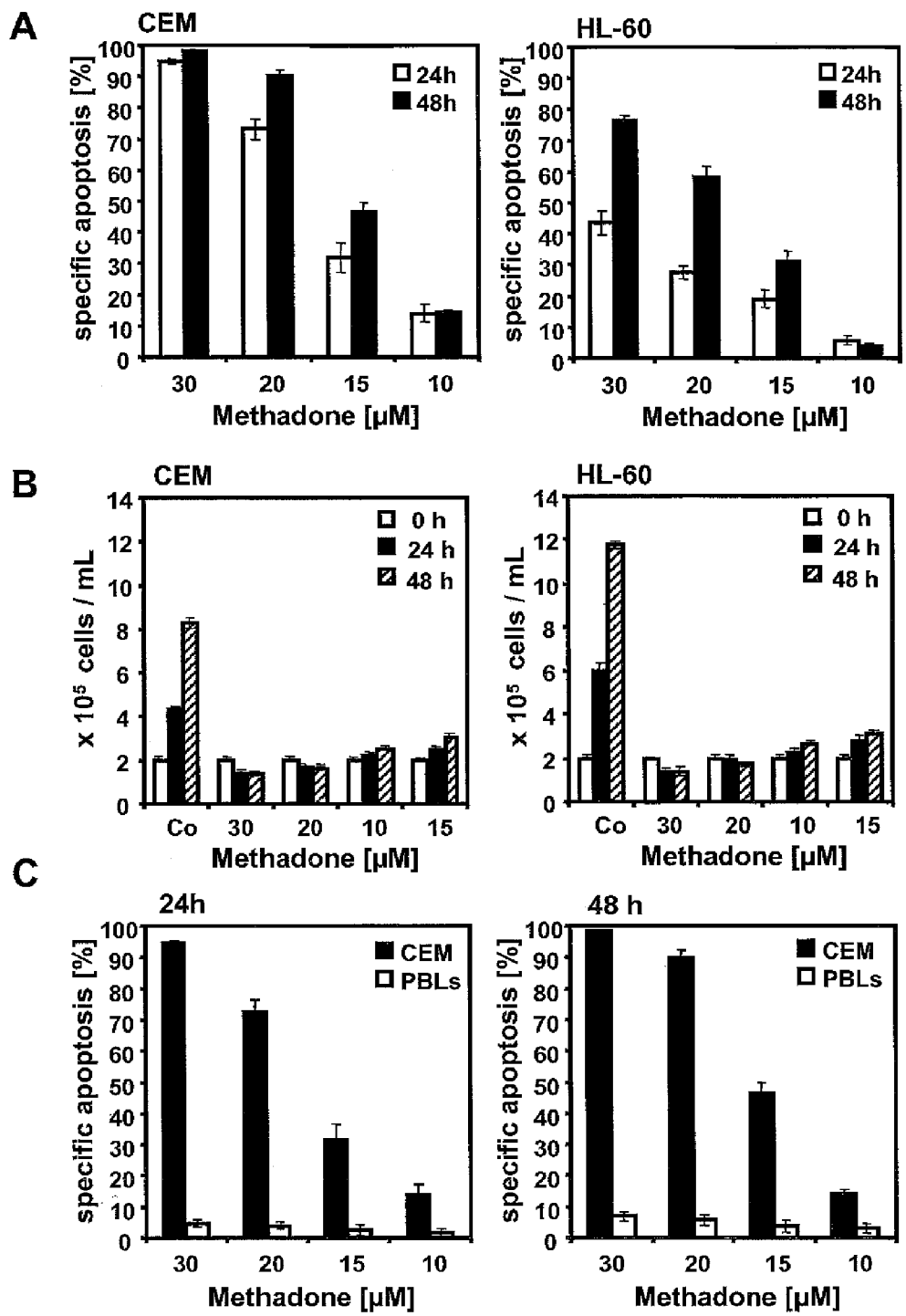

Friesen, C, et al., "Breaking chemo- and radioresistance with [213Bi]anti-CD45 antibodies in leukaemia cells.", Cancer Res, 2007, 67(5):1950-8.

Friesen, C. et al. Involvement of the CD95(APO-1/FAS) receptor/ligand system in drug-induced apoptosis in leukemia cells. Nat Med 1996 2(5):574-7.

Friesen, C. et al. "A critical role of glutathione in determining apoptosis sensitivity and resistance in leukaemia cells", Cell Death Differ 2004: 11(Suppl. 1), p. 73-85.

Friesen, C. et al. "Beta-irradiation used for systemic radioimmunotherapy induces apoptosis and activates apoptosis pathways in leukaemia cells", Eur J Nucl Med 2003: 30, 1251-61.

Hatsukari, I. et al., "Induction of early apoptosis marker by morphine in human lung and breast carcinoma cell lines", Anticancer Res. 2003, 23(3B), p. 2413-7.

Hengartner MO, "The biochemistry of apoptosis", Nature 2000, 407(6805), p. 770-6.

Heusch, WL et al., "Effects of bombesin on methadone-induced apoptosis in lung cancer cells", Cancer Lett 1999, No. 136, p. 177-85.

Kaufmann, SH et al. "Inductin of apoptosis by cancer therapy", Experimental Cell Research 2000, No. 256, p. 42-9.

Los, M. et al., "Cross-resistance of CD95- and durg-induced apoptosis as a consequence of deficient activation of caspases (ICE/Ced-3 proteases)", Blood, 1997, 90(8), p. 3111-29.

Milas, L. et al., "Targeting molecular determinants of tumour chemoradioresistance", Semin Oncol. 2005, No. 32, p. 78-81.

Nicoletti, I. et al., "A rapid and simple method for measuring thymocyte apoptosis bypropidium iodide staining and flow cytometry", Immunol Meth 1991, No. 139, p. 271-9.

Polakiewicy, RD et al., Mu/Opioid receptor activates signaling pathways implicated in cell survival and translational control@, J Biol. Chem, 1998, 273(36), 23534-41.

Lewis et al.: "Apparent Involvement of Opioid Peptides in stress-induced enhancement of Tumor Growth", in: Peptides, vol. 4, p. 635-638, 1983.

Lennon et al.: "The μ-Opioid Receptor in Cancer Progression", in: Anesthesiology, vol. 116, No. 4, p. 940-945, Apr. 2012.

Lennon et al.: "The Mu Opioid Receptor Promotes Opioid and Growth . . . ", in: PLOS ONE, vol. 9, Iss. 3, Mar. 2014.

Lin et al.: "Morphine inhibits doxorubicin-induced reactive oxygen species generation", in: Biochem. J. (2007), No. 406, p. 215-221.

Mao et al.: "The Effects of Anesthetics on Tumor Progression", in: Int. J Physiol Pharmacol 2013; 5(1):1-10.

Mathew et al.: "The novel Role of the Mu Opioid Receptor in Lung Cancer Progression . . . ", in: Anesthesia & Analgesia; vol. 112, No. 3, p. 558-567, Mar. 2011.

Moon, Timothy: "The Effect of Opiaties upon Prostatic Carcinoma Cell Growth", in: Biochemical and Biophysical Research Communications, vol. 153, No. 2, p. 722-727, Jun. 1988.

Melzig et. al.: "β-Endorphin stimulates Proliferation of small Cell Lung Carcinoma Cells in Vitro via Nonopioid Binding Sites", in Expermental Cell Research 219, p. 471-476, 1995.

Gupta et al.: "Morphine stimulates Angiogenesis by Activating Proangiogenic and Survival-promoting Signaling and promotes Breast Tumor Growth", in: Cancer Res 2002; 62; p. 4491-4498.

Ueda, Hiroshi and Yoshida, Akira: "Suppression of Cancer Cell Proliferation by Opioid Analgesics", in: Hematology & Oncology, 39 (3), p. 213-219, 1999.

Adams, JM and Cory,S: "The BcI-2 apoptotic switch in cancer development and therapy", in: Oncogene (2007), vol. 26, p. 1324-1337.

Lao, Paul N.: "The Effects of Opiates on the Lung", in: Clinical Reviews in Allergy and Immunology 1997, vol. 15, p. 291-305.

Sirika, K. et al.: "Pain Medication during terminal care of children with cancer", in: Journal of Pain and Symptom Management, 1998, vol. 15, No. 4, p. 220-226.

Schmidli, H. et al.: Population pharmacokinetics of imatinib mesylate in . . . , in: Clinical Pharmacology, 2005, vol. 60, No. 1, p. 35-44.

Hagen, N.A. et al.: "Sublingual methadone for the management of cancer-related breakthrough pain . . . ", Abstract, in: J. Palliat. Med, Apr. 10, 2007,, vol. 2, p. 331-337.

Centeno, C. et al.: "Intermittent subcutaneous methadone administration . . . ", in: J Pain Palliat Care Pharmacother, 2005, vol. 19, No. 2, p. 7-12.

\* cited by examiner

Patient 1

Patient 3

USE OF OPIOIDS OR OPIOID MIMETICS FOR THE TREATMENT OF RESISTANT CANCER PATIENTS

CROSS-REFERENCES TO RELATED APPLICATIONS

This application is the U.S. National Stage of International Application No. PCT1EP2009/1000584, filed Jan. 29, 2009, which designated the United States and has been published as International Publication No. WO 2010/012319 and which claims the priority of European Patent Application, Serial No. 08 013 741.7, filed Jul. 31, 2008, pursuant to 35 U.S.C. 119(a)-(d).

BACKGROUND OF THE INVENTION

The invention relates to novel strategies for the treatment of resistant cancer patients.

Anti-cancer therapies are frequently ineffective due to resistance of the tumor cells to radio- and/or chemotherapy. When the resistance is acquired during therapy, it often manifests either in a diminished amount of tumor regression for the same dose (either of the radiation or the cytotoxic substance) or an increased dose which is necessary for an equal amount of tumor regression. When, the resistance is intrinsic, i.e. not acquired or induced due to the anti-cancer treatment, the tumor cells already originally lack sensitivity to one or more anti-cancer drugs or ionizing radiation.

The chemosensitivity of cancer cells often vary on an individual basis. For pancreas carcinoma e.g. it is known, that only approximately 25% of all patients benefit from the anti-cancer drug gemcitabine. The other 75% are intrinsically resistant to this chemotherapy. Further examples for tumor cells with intrinsic chemo- and radioresistance are glioblastoma or melanoma cells.

The intrinsic or acquired resistance (or non-response) of tumor cells to radio- and/or chemotherapy can have multiple reasons and can—as exemplified above—vary on an individual basis. Despite intensive research the exact mechanisms still remain elusive. However, it is known that either a single mutation, e.g. at the drug substance binding site or within the cellular detoxification process, can be responsible for the lack of or reduced chemosensitivity. Also the manifestation of cross-resistances to several anticancer drugs often limits the efficacy of anticancer treatments.

Of significant clinical importance is the phenomenon of the so called multi-drug resistance (MDR). According to this concept, membrane proteins, namely members of the ATP binding cassette (ABC) transporter proteins, such as the P-glycoprotein or the multi-drug resistance associated proteins (MRP) are increasingly expressed, which leads to an enhanced efflux of drug substances through active transportation via the cell membrane. Patients exhibiting a multi-drug resistance most often are resistant to a wide spectrum of cytotoxic drugs.

Resistances are not limited to chemotherapeutics or anticancer drugs; cancer patients can also exhibit either an intrinsic or acquired resistance to ionising irradiation applied in radiotherapy. An intrinsic radioresistance is known e.g. from melanoma and glioblastoma cells.

Radioresistance may also be induced by exposure to small or fractionated doses of ionizing radiation. Several studies have documented this effect in vitro even in human cells as well as in several animal models. Different cellular radioprotection mechanisms may be involved, such as alterations in the levels of some cytoplasmatic and nuclear proteins, increased gene expression or DNA repair processes.

SUMMARY OF THE INVENTION

Thus in oncology there is a great need for novel strategies, which render cancer treatments more effective. In particular it is the objective of the present invention to provide novel means for treating cancer patients, which exhibit a resistance to conventional anticancer therapies, such as anticancer drugs (chemotherapy) or radiotherapy or for treating cancer patients with apoptose resistant cells.

This objective is solved by using opioids or opioid mimetics in the treatment of radiotherapy and/or chemotherapy resistant cancer patients, since now it was found that opioids capable of inhibiting the cell proliferation and or growth of cancer cells can overcome resistances in these cancer cells. Therefore these opioids provide novel strategies for treating patients, who so far are considered to be non-treatable or not effectively treatable by conventional therapeutic anticancer approaches. This group of alleged non-treatable cancer patients can also be called "non-responders", "poor-responder" or "non-chemosensitive" or "non-radiosensitive" cancer patients.

It was furthermore found that opioids and opioid mimetics can overcome apoptosis resistance of cancer cells, and thus can effectively be clinically applied as anticancer substances. In particular, most surprisingly, it was found that opioids—in particular methadone—were as effective as the conventional chemotherapy (e.g. doxorubicin) and radiation treatments against non-resistant (i.e. sensitive) leukaemia cells, and that normal peripheral blood lymphocytes survived after this treatment. Hence, according to one embodiment of the invention, opioids are also effective in killing tumor cells, but do not substantially affect normal healthy cells of the patient.

In the context of the present invention the term "opioid" is defined as a chemical heterogeneous group of natural, synthetic or semi-synthetic substances, working agonistic or antagonistic which all can bind to the well known opioid receptors, preferably to the μ opioid receptor and which are capable of arresting cancer cell proliferation. The group of opioids includes natural opiates such as alkaloids like morphine, dihydrocodein,)codeine and thebaine, as well as semi-synthetic opiates, derived from the natural opiates (e.g. hydromorphone, hydrocodone, oxycodone, oxymorphone, desomorphine, diacetylmorphine (Heroin), nicomorphine, dipropanoylmorphine, benzylmorphine and ethylmorphine), or fully synthetic opioids, such as fentanyl, pethidine and methadone, tramadol or propoxyphene. It also includes endogenous opioid peptides, which may be produced naturally in the body as endorphins, dynorphins or enkephalins but which can also be synthesized.

Opioids are known for their use as analgetics. The fact that opioid receptors, especially μ opioid receptors are involved in the activation of signalling pathways leading to apoptosis was previously known (Polakiewicz et al. 1998). in the past decade it was found that opioids can promote apoptosis (Hatsukari et al. 2003). It was further discussed to use opioids for the induction of apoptosis in small lung cancer cells (Heusch & Maneckjee 1999). However, the underlying mechanisms were not unrevealed, nor do those results suggest employing opioids for overcoming resistances to conventional anticancer treatments.

According to the invention the opioid is capable of inhibiting cancer cell proliferation and/or growth. This activity can include e.g. cytostatic or cytotoxic activity as well as arresting growth of cells and/or tumors. Cancer cell proliferation is the result of the inhibition of cell division. In particular opioids or opioid mimetics induce cell death in tumors. Cell death in the context of the invention includes all types of cells death. This can include necrotic as well as apoptotic cell death or autophagy. In one embodiment of the invention the cell death is induced by the activation of the caspases-dependent or caspases-independent pathway. However, opioids can induce cell death via various pathways. In a preferred embodiment of the invention, opioids induce apoptosis in cancer cells.

Generally, it is known, that apoptosis can be induced via two main biochemical pathways. The "death receptor pathway" (or extrinsic pathway) includes the TNF-receptor-induced (tumor necrosis factor) model and the Fas-receptor-induced model (the Fas-receptor is also known as Apo-1 or CD95). Bindings to these receptors result in the formation of death-inducing signalling pathways in the cell, including the activation of caspases-8. The "mitochondrial pathway" (or intrinsic pathway) involves the release of cytochrom c from mitochondria, binding of Apaf-1 and activation of pro-caspase-9. Several regulators are known to activate or deactivate the apoptosis pathways, such as the pro-apoptotic proteins Bax and Bak or the anti-apoptotic proteins Bcl-2, $Bcl_{XL}$ or XIAP.

In the context of the invention the term "opioid mimetics" is defined as a substance, which either indirectly or directly is capable to induce within the cancer cells substantially the same effect as opioids, in particular in view of the effects of opioids' binding to the opioid receptor (e.g. µ receptor) and/or the induction of cell death, in particular apoptosis via the mitochondrial pathway. The term "opioid mimetics" also includes substance, which lead to the over expression of opioid receptors, such as e.g. cocaine, and therewith indirectly induce cell death.

In one embodiment of the invention opioids or opioid mimetics induce apoptosis by one or more of the following mechanisms:
  i. cleavage of caspase-3 and PARP in the tumour cell
  ii. cleavage of caspase-9 and down regulation of XIAP
  iii. down regulation of $Bcl_{XL}$ According to a preferred embodiment of the invention, the opioid is a member of the methadone group, comprising D-/L-methadone, levomethadone, levacetylmethadol and piritramide. All these opioids can be used as salts. The racemic form of D-/L-methadone is preferably provided in form of a hydrochloride. In a preferred embodiment of the invention, the opioid methadone induces apoptosis in cancer cells via the mitochondrial pathway.

According to the invention, the terms "resistance", "radioresistance" or "chemoresistance" are defined as a reduced sensitivity of a cancer cell to at least one conventional cancer therapy, i.e. either an anticancer drug or radiotherapy. A patient suffering from such a cancer is determined as a "resistant" cancer patient. Since the resistance can be intrinsic or acquired the observed reduction in sensitivity is either compared to fully sensitive "normal" cancer cells, which are responsive to the therapeutically effective dosage of the applied anticancer drug and/or radiation compared to the original sensitivity upon therapy onset. In the later case the resistance manifests either in a diminished amount of tumour regression for the same dose (either of the radiation or the anticancer drug) or an increased dose which is necessary for an equal amount of tumor regression.

In a particularly preferred embodiment the opioids or opioid mimetics are used to treat cancer patients who exhibit one or more of the subsequent resistances:
apoptosis resistance
multi-drug resistance
anticancer drug resistance
cytotoxic drug resistance
resistance to reactive oxygen species
resistance to DNA-damaging agents
resistance to toxic antibodies
doxorubicin resistance
single or cross resistance, in particular to one or more of the following drug substances: methotrexate, cytarabine, cisplatin, etoposide, vincristine, paclitaxel (taxol), carboplatin, teniposide, dexamethasone, prednisolone, cyclophosphamide, iphosphamide, doxorubicin, epirubicin, daunorubicin, mercaptopurine, fludarabine, 5-fluoruracil
irradiation resistance (e.g. alpha, beta, gamma or Auger electrons)

Accordingly, in the context of the present invention a "resistance" can either be total or partly; in other words, the patients considered treatable according to the invention can exhibit a reduced sensitivity or even a full lack of sensitivity to conventional anticancer treatments. These patients can also be determined as "non-responders" or "poor-responders".

A further synonym for a "resistant" cancer or tumor is a "refractory" type of cancer, which can also be either completely or partly refractory. Intrinsic resistance can thus also be determined as a "primary refractory cancer". A particular form of refractory or resistant cancer cells ar the so called "kinetically refractory cells"; a phenomenon known e.g. from leukaemia cells, when the cells are at first killed, but reproduce fast that an effective treatment is hardly possible.

As used in the context of the present invention the term "conventional" treatment or therapy refers to the currently accepted and widely used therapeutic treatment of a certain type of cancer, based on the results of past researches and/or regulatory approval.

Conventional anticancer drugs include cytotoxic and cytostatic agents, which kill the cancer cells or reduce and/or stop their growth or proliferation. The modes of action of these anticancer drugs can vary; examples are antimetabolites (e.g. cytarabine, methotrexate, mercaptopurine or clofarabine), DNA cross-linking agents (e.g. cisplatine and its derivates), DNA intercalating substances (e.g. doxorubicin), Topoisomerase poisons (e.g. etoposide), kinase inhibitors (e.g. cetuximab), steroids (e.g. dexamethasone) or mitotic inhibitors (e.g. vincristine). One example for a conventional anticancer treatment of leukaemia is the administration of doxorubicin.

The conventional radiotherapy can also include radiation therapy, which means the use of high-energy radiation from x-rays, alpha, beta and gamma rays, Auger electrons, Ultraviolet rays, neutrons, protons, and other sources to kill cancer cells and shrink tumors. Radiation may originate from an outside the body device (external-beam radiation therapy), or it may originate from radioactive sources placed in the body in the vicinity of the cancer cells (internal radiation therapy). Systemic radiation therapy uses a radioactive substance, such as a radiolabeled monoclonal antibody, that travels in the blood stream to the target tissue. Radioresistant cancer cells do not or only partly respond to these treatments.

As outlined in detail above, according to one embodiment of the invention opioids or the opioid mimetics are applied for overcoming or "breaking" the intrinsic or acquired resistance of cancer cells to conventional anticancer treatments and/or radiation treatment or apoptosis resistance. In one embodiment of the invention cancer cells considered treatable according to the invention express an opioid receptor, in particular the µ opioid receptor.

In a further embodiment the group of cancers include, but is not limited to leukaemia, breast cancer, glioblastoma, prostate cancer, lung cancer, non-small cell lung cancer (NSCLC), brain cancer, colon cancer, colorectal cancer.

Examples for cancer types, considered to be treatable according to the invention, with intrinsic resistance to irradiation are glioblastoma, melanoma or pancreas cancer cells. Breast cancer, bladder cancer or leukaemia are often resistant to chemotherapeutics. Examples of cancer types which often acquire resistance are melanoma, colon carcinoma, brain tumors glioblastoma, brain cancer, pancreatic cancer, liver cancer, ovarian cancer, cancer of mamma, lung cancer, chronic leukaemia or osteosarkoma.

In a further embodiment of the invention, the opioids or opioid mimetics can be used in combination—i.e. as a composite—with conventional anticancer substances or treatments, e.g. cytostatic or cytotoxic substances or radiotherapy. The opioids or opioid mimetics can be combined for example with natural and/or synthetic anticancer substances, natural and/or synthetic cytotoxic substances, antibiotics, cytotoxic antibodies, hormones, psycho-pharmaca, naturally or genetically modified organisms and substances from organisms (e.g. plants, microorganisms, fruits), substances for pain, and/or different sorts of radiation unbound or bound to substances (e.g. antibodies). The patient can either be resistant or not resistant to this treatment.

A "composite" means a pharmaceutical preparation comprising a therapeutically effective amount of any of the opioids or opioid mimetics (component A) as defined according to the invention and at least one further anticancer substance (component B). This "composite" can constitute a single composition or at least two compositions, which can be administered to the patients either concomitantly or subsequently. The above mentioned substances are preferably combined with methadone.

The composite of the invention can be advantageous for the effective treatment of cancer cells, since it can exhibit synergistic effects compared to the single compositions. In particular composite with methadone as component A and one of the agents as component B as follows is possible: methotrexate, cytarabine, cisplatine, etoposide, vincristine. Moreover combinatorial treatment also comprising irradiation treatments is possible.

In a preferred embodiment of the invention opioids are used to treat either resistant or sensitive non-solid cancers, i.e. all haematological malignancies affecting blood, bone marrow and lymph nodes, including acute lymphoblastic leukaemia, B-cell lymphatic leukaemia, acute myeloid leukaemia, chronic myeloid leukaemia, chronic lymphocytic leukaemia and all pro-forms of leukaemias, hairy cell leukaemia, Hodgkin's disease, Non-Hodgkin lymphoma and multiple myeloma.

EXAMPLE 1

Use of Methadone for the Treatment of Leukaemia Cells and Especially for the Treatment of Leukaemia Cells, which Anticancer Drugs Commonly used in Conventional Therapies Failed to Kill Drugs and Reagents D, L-methadone hydrochloride (methadone, Sigma, Taufkirchen, Germany) was freshly dissolved in sterile distilled water prior to each experiment to ensure constant quality of the preparations.

Cell Culture

The human myeloid leukaemia cell line HL-60 and the human lymphoblastic leukaemia T-cell line CEM were grown in RPMI 1640 (GIBCO, Invitrogen, Karlsruhe, Germany) containing 10% fetal calf serum (Biochrom, Berlin, Germany), 10 mM HEPES, pH 7.3 (Biochrom), 100 U/mL penicillin (GIBCO), 100 µg/mL streptomycin (GIBCO) and 2 mM L-glutamine (Biochrom) at 37° C. and 5% $CO_2$. $CEM^{CD95R}$ are resistant to 1 µg/mL anti-CD95 (Friesen et al. 1996) and $CEM^{DOXOR}$ are resistant to 0.1 µg/mL doxorubicin (Friesen et al. 2004). $CEM^{CD95R}$ is apoptosis-resistant and multi-drug resistant. $CEM^{CD95R}$ is cross-resistant to several anticancer drugs such as methotrexate, cytarabine, cisplatine, etoposide, vincristine and to gamma- and beta-irradiation (Friesen et al. 1996, Los et al. 1997, Friesen et al. 2007). All cell lines used in this study were mycoplasma free.

Induction of Apoptosis

Leukaemia cells ($1 \times 10^5$ cells/mL) were treated with 30, 20, 15, 10 µM methadone in 150 mL flasks or 96 well plates. After 24 h and 48 h, quantification of apoptosis was measured by flow cytometry as described (Carbonari et al. 1994, Friesen et al. 2003). In brief, to determine apoptosis, cells were lysed with Nicoletti-buffer containing 0.1% sodium citrate plus 0.1% Triton X-100 and propidium iodide 50 µg/mL as described by Nicoletti et al. (1991). The percentage of apoptotic cells was measured by hypodiploid DNA (subG1) or FSC/SSC analysis (Nicoletti et al. 1991, Carbonari et al. 1994). Propidium iodide (PI) stained nuclei or forward scatter/side scatter (FSC/SSC) profiles of cells were analyzed by flow cytometry (FACSCalibur, Becton Dickinson, Heidelberg, Germany).

Isolation of Peripheral Blood Lymphocytes

Peripheral blood lymphocytes (PBLs) were isolated from fresh blood of healthy persons. PBLs ($1 \times 10^6$ cells in 1 mL) were treated with 30, 20, 15, 10 µM methadone in 96 well plates. After 24 h and 48 h quantification of apoptosis was measured by flow cytometry as described (Carbonari et al. 1994).

Inhibition of Methadone Induced Caspases Activation by zVAD.fmk

Inhibition of caspases activation was performed as previously described (Friesen et al. 2007). In brief, the broad spectrum tripeptide inhibitor of caspases zVAD.fmk (benzoyl carbonyl-Val-Ala-Asp-fluoromethyl ketone, Enzyme Systems Products, Dubli, USA) was used at a concentration of 50 µmol/L. HL-60 and CEM cells were preincubated with zVAD.fmk 1 h before methadone treatment. After 24 h and 48 h the percentage of apoptotic cells was measured by hypodiploid DNA (subG1) or FSC/SSC analysis. Propidium iodide (PI) stained nuclei (Nicoletti et al. 1991) or forward scatter/side scatter (FSC/SSC) profile of cells (Carbonari et al. 1994) were analyzed by flow cytometry (FACSCalibur, Becton Dickinson, Heidelberg, Germany).

Western Blot Analysis

Western blot analyses were done as described (Friesen et al. 2004, Friesen et al. 2003). Immunodetection of PARP, caspase-3, caspase-9, caspase-8, XIAP, CD95, CD95-L, Bax, Bcl-$x_L$ and β-actin was done using rabbit anti-PARP polyclonal antibody (1:5000, Roche), mouse-anti-caspase-3 monoclonal antibody (1:1000, Cell-Signalling), mouse-anti-caspase-8 monoclonal antibody (1:1000, Cell-Signalling), rabbit- anti-active-caspase-9 polyclonal antibody (1:1000, Cell-Signalling), mouse-anti-XIAP monoclonal antibody (1:1000, Transduction-Laboratories, Lexington, Ky.), mouse-anti-Fas (anti-CD95) monoclonal antibody (1:1000, Transduction-Laboratories), mouse-anti-Fas ligand (anti-CD95-ligand) monoclonal antibody (1:250, BD, Pharmingen), rabbit-anti-Bax polyclonal antibody (1:250, Oncogene, Cambridge), rabbit-anti-Bcl-$X_{S/L}$. polyclonal antibody (1:1000, Santa-Cruz-Biotechnology, Santa-Cruz, Calif.), rabbit-anti-p21 polyclonal antibody (1:1000, Santa-Cruz), and mouse anti-β-actin monoclonal antibody (Sigma). Peroxidase-conjugated goat-anti-mouse IgG or peroxidase-conjugated goat-anti-rabbit IgG (1:5000, Santa-Cruz) as secondary antibody were used for the enhanced chemoluminescence system (ECL, Amersham-Pharmacia, Freiburg, Germany). Equal protein loading was controlled by β-actin detection.

Methadone Induces Cell Killing in CEM and HL-60 Leukaemia Cells through Apoptosis with Non-Toxic Effects in Non-Leukemic PBLs In leukaemias and solid tumours anticancer drugs have been shown to induce apoptosis and to inhibit proliferation (Kaufmann & Earnshaw 2000). Therefore, it was analyzed if the therapeutic opioid drug methadone can also inhibit proliferation and trigger apoptosis in the human lymphoblastic leukaemia T-cell line CEM and the human myeloid leukaemia cell line HL-60 comparable to the well-known established anticancer drugs (FIG. 1A, B). 24 h and 48 h after treatment with different concentrations of methadone (30, 20, 15, 10 µM) a strong induction of apoptosis (FIG. 1A) and a strong inhibition of growth (FIG. 1B) were detected in CEM and HL-60 cells. It was next analyzed if methadone induces apoptosis also in non-leukaemic peripheral blood lymphocytes (PBLs) (FIG. 1C). Isolated PBLs were incubated with different concentrations of methadone (30, 20, 15, 10 µM). 24 h and 48 h after methadone treatment it was found that methadone could not kill PBLs at comparable concentrations using for the treatment of leukaemia cells such as CEM (FIG. 1C). This demonstrates that methadone induces apoptosis in leukaemia cells with non-toxic effects on non-leukaemic PBLs.

Methadone Breaks Doxorubicin-Resistance, CD95-Resistance, and Multidrug-Resistance in Leukaemia Cells Resistance to anticancer drugs is a limiting factor in treatment of leukaemia and tumour patients (Bergman & Harris 1997, Friesen et al. 2003). It has been found that methadone exhibits a potent anti-leukaemic activity and efficiently kills leukaemia cells. Therefore it was analyzed if methadone can also induce cell death in doxorubicin-resistant leukaemia cells, which were apoptosis-resistant. Doxorubicin-resistant CEM leukaemia cells (CEM$^{DoxoR}$) were treated with different concentrations of methadone (30, 20, 15, 10 µM). 24 h and 48 h after methadone treatment, cell death was measured by flow cytometry. After treatment with 30, 20, 15 µM methadone, a strong induction of apoptosis was measured in doxorubicin-resistant cells CEM$^{DoxoR}$, which was similar to that in sensitive leukaemia cells CEM (FIG. 2), indicating that methadone overcomes doxorubicin-resistance and apoptosis-resistance.

Figure 2:
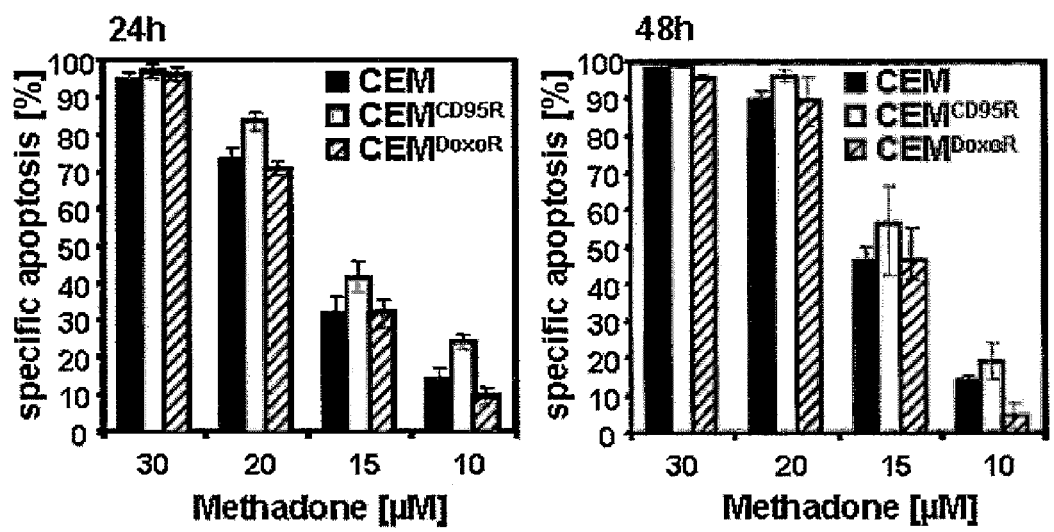

It was next examined if methadone can also kill leukaemia cells, which were multidrug-resistant. Therefore CD95-resistant leukaemia cells CEM$^{CD95R}$, which were resistant to several anticancer drugs such as etoposide, cisplatine, methotrexate, cytarabine, doxorubicin, vincristine, were treated with different concentrations of methadone (30, 20, 15, 10 µM). After treatment with 30, 20, 15 µM methadone, a strong induction of apoptosis in CD95-resistant leukaemia cells CEM$^{CD95R}$ was measured after 24 h and 48 h, which was similar to that in sensitive leukaemia cells CEM (FIG. 2). This suggests that methadone induces not only a strong induction of apoptosis in sensitive leukaemia cells, but it also kills doxorubicin- and CD95-resistant leukaemia cells, which commonly used anticancer drugs failed to kill (Friesen et al. 1996, Los et al. 1997).

Methadone Induces Caspases-Dependent Cell Death and Activates Mitochondria in Sensitive, Doxorubicin-Resistant, CD95-Resistant, and Multidrug-Resistant Leukaemia Cells Methadone induces apoptosis in sensitive and in resistant leukaemia cells with unknowing molecular mechanisms. Therefore, the mechanism and effector molecules which may be altered by methadone-triggered cell death in leukaemia cells were to be examined.

Caspases play a critical role in apoptosis induction by anticancer drugs (Kaufmann & Earnshow 2000, Hengartner 2000). Therefore Western blot analysis was used to examine if methadone activates caspases in HL-60 and CEM leukaemia cells as well as in doxorubicin-resistant leukaemia cells CEM$^{DoxoR}$, which were apoptosis-resistant and in CD95-resistant leukaemia cells CEM$^{CD95R}$, which were multidrug-resistant and apoptosis-resistant. After treatment with different concentrations of methadone (20, 15 µM) caspase-3, and PARP were cleaved in HL-60 and CEM leukaemia cells (FIG. 3A) as well as in doxorubicin-resistant leukaemia cells CEM$^{DoxoR}$ and in CD95-resistant leukaemia cells CEM$^{CD95R}$ (FIG. 3B). Activation of caspase-8, which anticancer drugs have shown to induce in leukaemia cells, was not found after methadone treatment. To investigate the critical role of methadone in activation of caspases, CEM and HL-60 cells were preincubated with the broad spectrum inhibitor of caspases zVAD.fmk. Incubation with zVAD.fmk almost completely inhibited methadone-induced apoptosis (FIG. 3C) suggesting that caspases are central for methadone-induced apoptosis in leukaemia cells.

Figure 4:
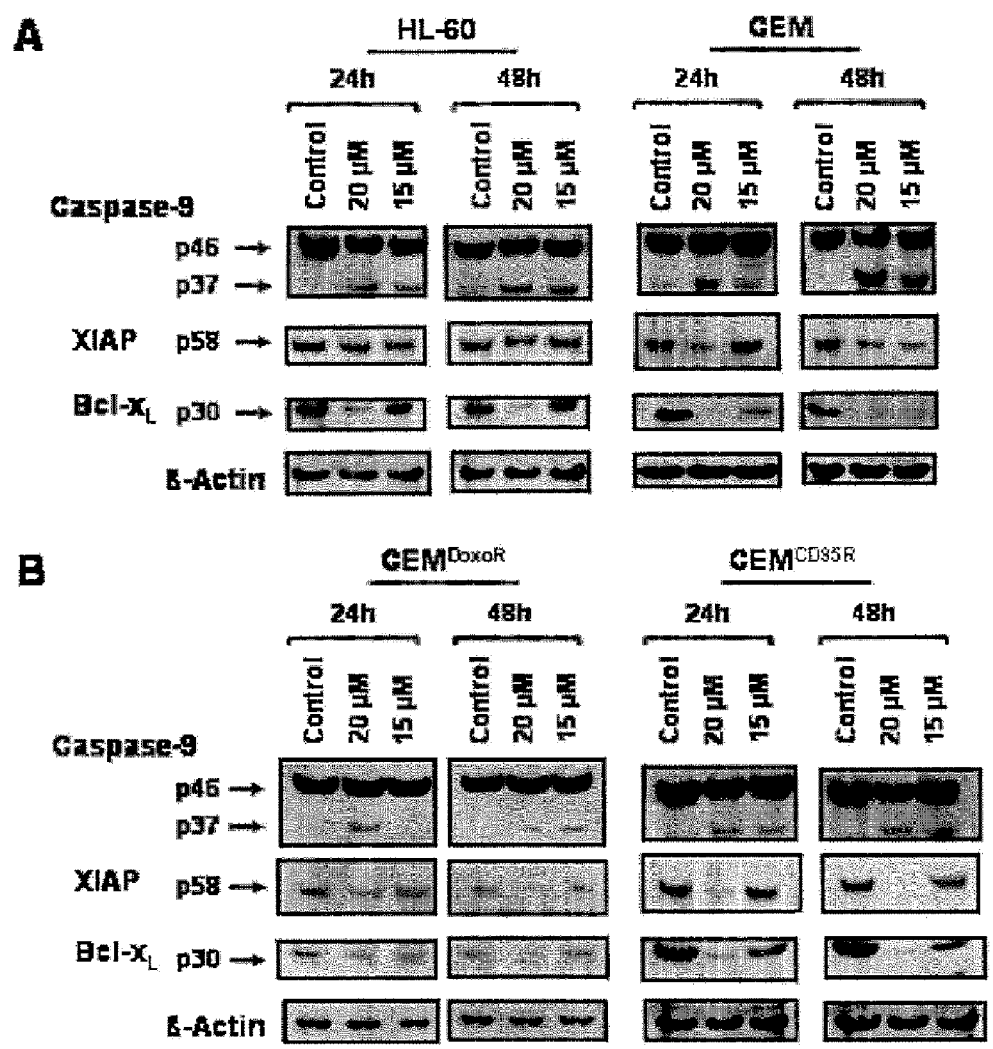

Anticancer-drugs have been shown to activate the mitochondrial pathway as well as the ligand/receptor pathway in leukaemia and tumour cells (Kaufmann & Earnshow 2000). It was investigated if mitochondria could also play a role methadone-induced apoptosis in leukaemia cells. CEM, HL-60, doxorubicin-resistant leukaemia cells CEM$^{DoxoR}$ and CD95-resistant leukaemia cells CEM$^{CD95R}$ were treated with different concentrations of methadone (20, 15 µM) (FIG. 4). After 24 h and 48 h a strong cleavage (37 kDa fragment) of caspase-9 and a strong down regulation of the caspases inhibiting protein XIAP (X-linked inhibitory-of-apoptosis protein) was found in HL-60 and CEM leukaemia cells (FIG. 4A) as well as in doxorubicin-resistant leukaemia cells CEM$^{DoxoR}$ and in CD95-resistant leukaemia cells CEM$^{CD95R}$ (FIG. 4B), which were multidrug- and apoptosis-resistant.

Mitochondrial changes are regulated by pro- and anti-apoptotic Bcl-2 family members. After 24 h and 48 h a strong down regulation of Bcl-$x_L$ were found in HL-60 and in CEM leukaemia cells (FIG. 4A) as well as in doxorubicin-resistant leukaemia cells CEM$^{DoxoR}$ and in CD95-resistant leukaemia cells CEM$^{CD95R}$ (FIG. 4B) after treatment with different concentrations of methadone (20, 15 µM). Up regulation of Bax was not found after methadone treatment in leukaemia cells.

Furthermore, up regulation of death-inducing ligands and death-inducing receptors such as CD95, which anticancer drugs have shown to up regulate, were not found after methadone treatment in leukaemia cells (data not shown). This indicates that methadone induces apoptosis by directly activation of the intrinsic mitochondrial pathway in sensitive as well as in resistant leukaemia cells.

EXAMPLE 2

Methadone Induces Apoptosis in Glioblastoma Cells

Glioblastoma is the most aggressive and the most common type of primary brain tumours. Glioblastoma cells are known to be highly resistant to chemotherapeutics and irradiation. Treatment may involve chemotherapy and radiotherapy but these are only palliative measures and do not provide a cure. Moreover, many drugs cannot cross the blood brain barrier and are therefore useless in the treatment of glioblastoma. Methadone is able to cross the blood-brain barrier. The effect of methadone on glioblastoma cells was examined. Furthermore, the effect of methadone in combination with therapeutical concentrations of doxorubicin on glioblastoma cells was tested.

The human glioblastoma cell line A172 was grown in DMEN (Invitrogen, Karlsruhe, Germany) containing 10% fetal calf serum (Biochrom, Berlin, Germany), 10 mM HEPES, pH 7,3 (Biochrom), 100 U/mL penicillin (Invitrogen), 100 µg/mL streptomycin (Invitrogen) and 2 mM L-glutamine (Biochrom) at 37° C. and 5% $CO_2$.

Before methadone treatment, glioblastoma cells were seeded in a density of 7000 cells/cm² and treatment was performed 24 h after cell seeding.

Glioblastoma cells A172 (7000 cells/cm²) were treated with 30, 20 µg/mL methadone in 75 cm² flasks. After 120 h, 144 h and 168 h quantification of apoptosis was measured by flow cytometry. To determine apoptosis, cells were lysed with Nicoletti buffer containing 0,1% sodium citrate plus 0,1% Triton X-100 and propidium iodide 50 µg/mL. Propidium iodide (PI) stained nuclei were analysed by flow cytometry (FACSCalibur, Becton Dickinson, Heidelberg, Germany).

Figure 5:
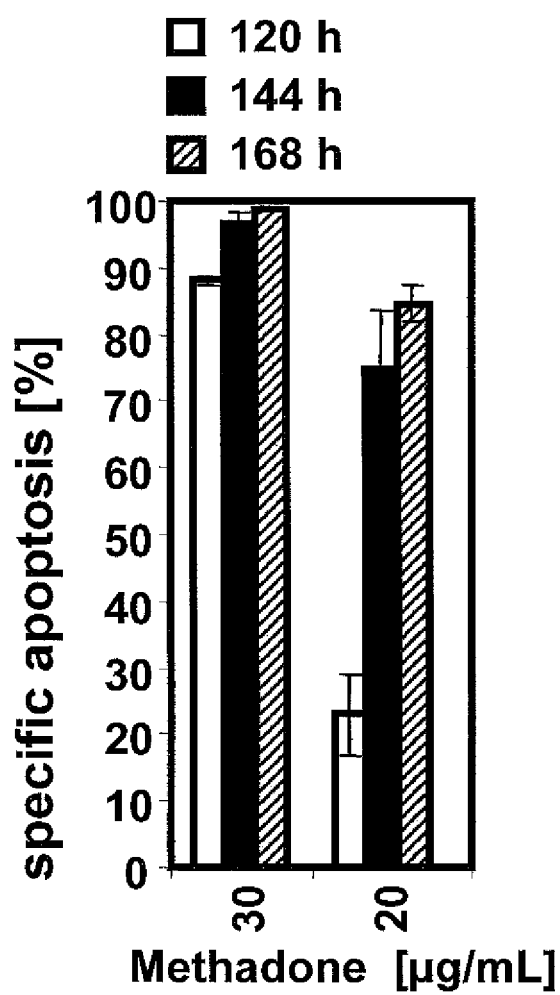

After 120 h, 144 h and 168 h, the percentages of apoptotic cells were measured by hypodiploid DNA analysis. The percentage of specific cell death was calculated as follows: 100×(experimentally dead cells (%)—spontaneous dead cells in cell medium (%)/(100%—spontaneous dead cells in medium, (%)). Treatment with methadone resulted in more than 20% dead cells after 120 h and more than 80% dead cells after 168 h after treatment with 20 µg/mL methadone. Treatment with methadone resulted in more than 85% dead cells after 120 h and nearly 100% dead cells after 168 h after treatment with 30 µg/mL methadone (FIG. 5). Similar results were obtained in tree independent experiments. This demonstrates that methadone induces high rates of apoptosis in glioblastoma cells.

EXAMPLE 3

Methadone Shows Synergistic Effects in Combination with Doxorubicin for the Induction of Apoptosis in Glioblastoma Cells Glioblastoma cells A172 (7000 cells/cm²) were treated with a therapeutical concentration of 0.1 µg/mL doxorubicin (doxorubicin, white columns), with a low concentration of 1 µg/mL methadone (methadone, black columns), and with 0.1 µg/mL doxorubicin in addition of 1 µg/mL methadone (doxorubicin+methadone, hatched columns). After 72 h quantification of apoptosis was measured by flow cytometry. To determine apoptosis, cells were lysed with Nicoletti-buffer containing 0.1% sodium citrate plus 0.1% Triton X-100 and propidium iodide 50 µg/mL. Propidium iodide (PI) stained nuclei were analyzed by flow cytometry (FACSCalibur, Becton Dickinson, Heidelberg, Germany).

Figure 6:
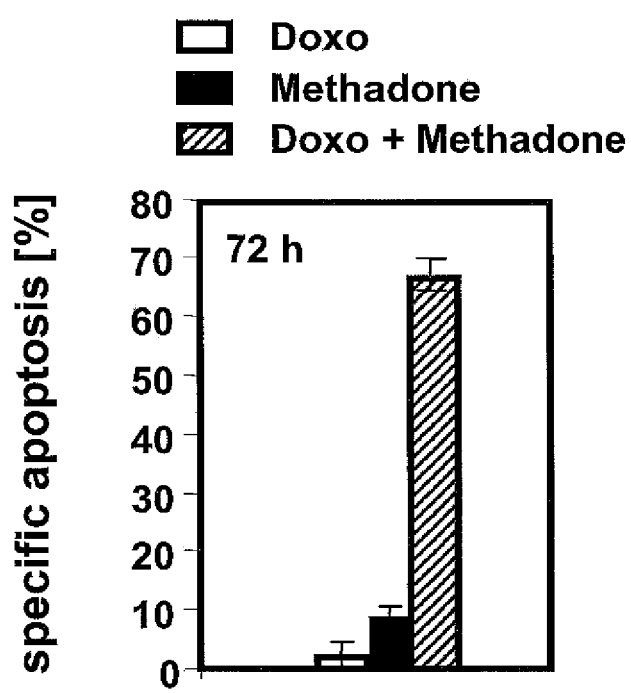

The combination of a therapeutical concentration of doxorubicin with low concentrations of methadone had a strong apoptotic effect on the glioblastoma cells tested (FIG. 6). This assay shows, that methadone reveals synergistic effects when applied together with other chemotherapeutics, here doxorubicin.

EXAMPLE 4

Induction of Apoptosis in Leukaemia Cells using Cocaine

CEM (white column) and HL-60 (black column) cells were treated with 1000 µg/mL of cocaine. After 48 h the percentages of apoptotic cells were measured by hypodiploid DNA analysis. The percentage of specific cell death was calculated as follows: 100×(experimental dead cells (%)—spontaneous dead cells in medium (%))/(100%—spontaneous dead cells in medium (%)). Data are given as mean of triplicates with a standard deviation (SD) of less than 10%. Similar results were obtained in three independent experiments.

Figure 7:
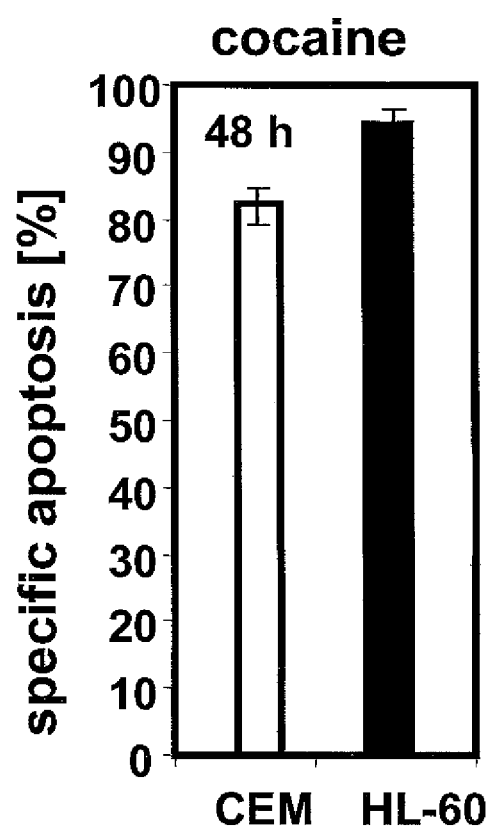

Results indicated that cocaine is able to induce apoptosis in CEM cells, as shown in FIG. 7.

EXAMPLE 5

Induction of Apoptosis in Cancer Cells Isolated from Patients ex vivo using D,L-Methadone alone or in Combination with Fludarabine B-ALL (B-Cell lymphatic leukaemia) and CLL (chronic lymphatic leukaemia) cells were isolated from patients ex viva. These cells were treated with different concentrations of D,L-methadone or D,L-methadone in addition of fludarabine.

In a first study, B-ALL (B-Cell lymphatic leukaemia) cells (50000 cells/100 µl) were treated with 30, 20, 15, 10 M methadone. After 48 h and 72 h quantification of apoptosis was measured by flow cytometry. Results indicated that already 10 µM methadone were sufficient to induce apoptosis in up to over 80% of the cells treated for 72 h (see FIG. 8).

In a second study, CLL (chronic lymphatic leukaemia) cells (50000 cells/200 µl) were treated with 30, 10, 5, 3, 1, 0.5, 0.3 and 0.1 µg/mL methadone alone or in addition of 0.1 µM fludarabine. After 24 h and 48 h quantification of apoptosis was measured by flow cytometry. Results indicated that apoptosis was induced in 100% of the cells already after 24 h, when combining 3 µg/mL methadone with 0.1 µM fludarabine (see FIG. 9).

In a third study, CLL (chronic lymphatic leukaemia) cells (50000 cells/200 µl) were treated with 30, 10, 5, 3, 1, 0.5, 0.3, 0.1 µg/mL methadone alone or in addition of 0.1 µM fludarabine. After 24 h and 48 h quantification of apoptosis was measured by flow cytometry. Results indicated that apoptosis was induced in nearly 50% of the cells after 48 hours, when combining 3 µg/mL methadone with 0.1 µM fludarabine. Apoptosis was induced in more than 90% of the cells after 48 h, when combining 30 µg/mL methadone with 0.1 µM fludarabine (see FIG. 10).

Thus, as suggested by these studies, methadone alone or in combination with a cytostatic treatment is successful in cancer cells isolated from patients ex vivo.

EXAMPLE 6

Induction of Apoptosis in Leukaemia Cells using Buprenorphine in Combination with Doxorubicin Buprenorphine was used successfully in combination with doxorubicin to induce apoptosis in HL-60 leukaemia cells in vitro. Buprenorphine is a semi-synthetic opioid drug, also used as analgesic. It is a partial µ-opioid receptor agonist.

Human acute myeloid leukaemia HL-60 cell line (5000 cells/100 µl) were treated with 30,10, 5, 3, 1, 0.5, 0.3, 0.1 µg/mL buprenorphine alone or in addition of 0.003 µg/mL or 0.001 µg/mL doxorubicin. After 144 h or 168 h quantification of apoptosis was measured by flow cytometry.

Results indicated that 20 µg/mL buprenorphine were sufficient to induce apoptosis in more than 90% of the cells after 144 h. The same result was obtained when adding 0.003 µg/mL doxorubicin. Apoptosis was induced in nearly 100% of the cells when combining 10 μg/mL buprenorphine with 0.003 μg/mL doxorubicin and incubating the cells for 168 h (see FIG. 13).

EXAMPLE 7

Induction of Apoptosis in Leukaemia Cells using Fentanyl in Combination with Doxorubicin Fentanyl was used successfully in combination with doxorubicin to induce apoptosis in CEM leukaemia cells in vitro. Fentanyl is a synthetic opioid, which is frequently used as analgesic in the treatment of cancer pain. Fentanyl is a μ opioid receptor agonist.

Human T-Cell leukaemia CEM cell line (10000 cells/100 μl) were treated with 30,10, 5, 3,1, 0.5, 0.3, 0.1 μg/mL fentanyl alone or in addition of 0.02 μg/mL doxorubicin. After 48 h and 72 h quantification of apoptosis was measured by flow cytometry.

Figure 14:
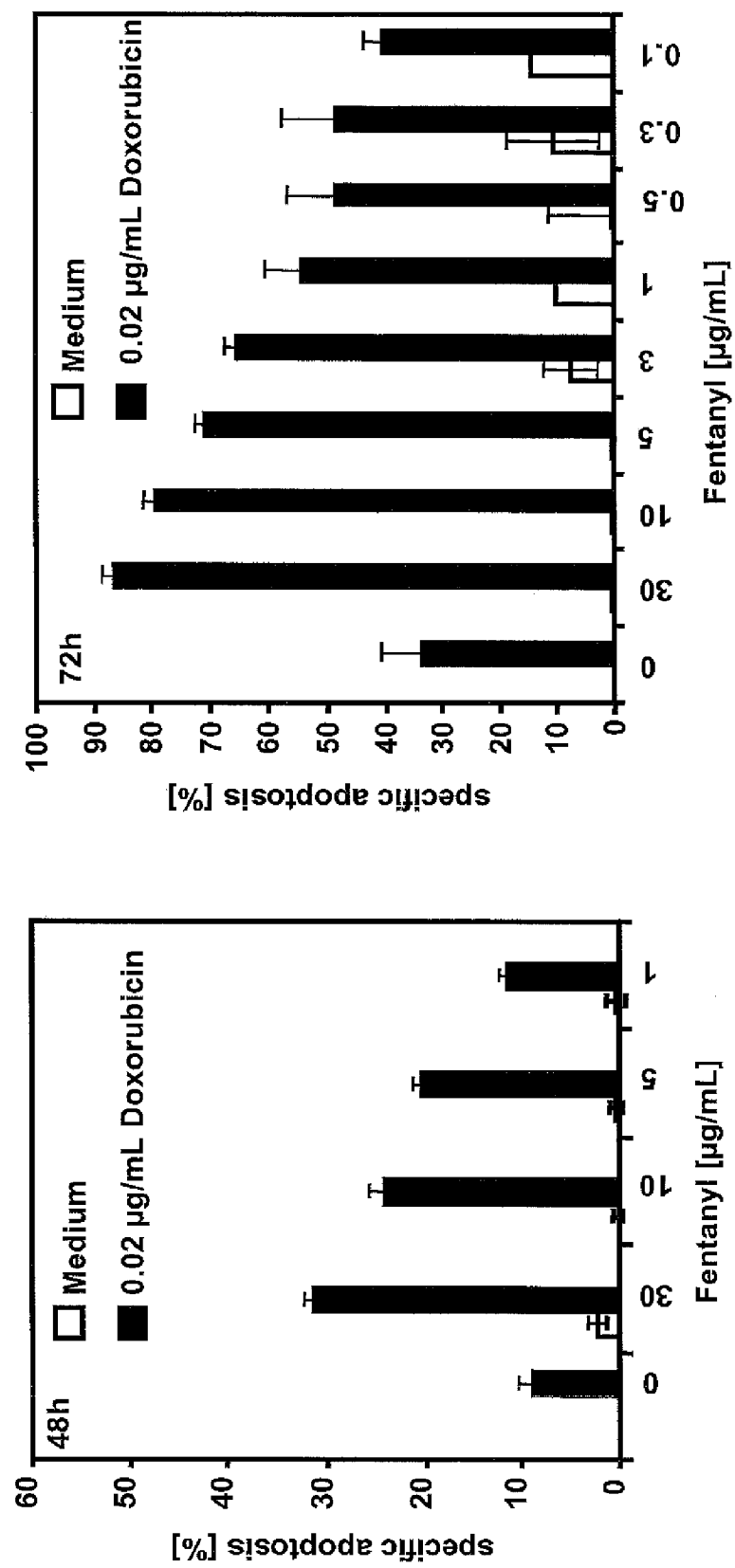

Results indicated that fentanyl successfully induced apoptosis in more than 85% of the cells after 72 h, when combining 30 μg/mL fentanyl with 0.02 μg/mL doxorubicin (see FIG. 14).

EXAMPLE 8

Induction of Apoptosis in Leukaemia Cells using Morphine

Morphine was used successfully alone and in combination with doxorubicin for the induction of apoptosis in HL-60 leukaemia cells. Morphine is an opiate which is currently used as analgesic in the treatment of cancer pain. Morphine is a μ opioid receptor agonist.

In a first study, human acute myeloid leukaemia HL-60 cells (5000 cells/100 μl) were treated with 30,10, 5, 3, 1, 0.5, 0.3, 0.1, 0.03, 0.01 μg/mL morphine. After 120 h or 144 h quantification of apoptosis was measured by flow cytometry. Results indicated that after 144 h apoptosis was induced in 40% of the cells when applying 40 μg/mL morphine see FIG. 15).

In a second study, human acute myeloid leukaemia HL-60 cells (5000 cells/100 μl) were treated with 1, 0.5, 0.3, 0.1, 0.03, 0.01 μg/mL morphine. After 96 h, 120 h, 144 h and 168 h quantification of apoptosis was measured by flow cytometry. Results indicated that after 168 h apoptosis was induced in more than 50% of the cells, when applying 1 μg/mL morphine (see FIG. 16).

In a third study, human acute myeloid leukaemia HL-60 cells (5000 cells/100 μl) were treated with 30,10, 5, 3, 1, 0.5, 0.3, 0.1 μg/mL morphine alone or in addition of 0.003 μg/mL or 0.001 μg/mL doxorubicin. After 168 h quantification of apoptosis was measured by flow cytometry. Results indicated that apoptosis was induced in 50% of the cells when applying 1 μg/mL morphine in combination with 0.001 μg/mL doxorubicin (see FIG. 17).

Thus, as suggested by these studies, the opiate and p receptor agonist morphine can be used successfully to induce apoptosis in leukaemia cells.

The Following Literature Cited Herein is Incorporated by Reference

Bergmann J P, Harris D. Radioresistance, chemoresistance and apoptosis resistance. Radiation Oncology 1997; 27:47-57.

Carbonari M, Cibati M, Cherchi M, et al. Detection and characterization of apoptotic peripheral blood lymphocytes in human immunodeficiency virus-infection and cancer chemotherapy by a novel flow immunocytometric method. Blood 1994; 83:1268-77.

Friesen C, Glatting G, Koop B, et al. Breaking chemo- and radioresistance with [$^{213}$Bi]anti-CD45 antibodies in leukaemia cells. Cancer Res 2007; 67(5):1950-8.

Friesen C, Herr I, Krammer P H, Debatin K M. Involvement of the CD95 (APO-1/FAS) receptor/ligand system in drug-induced apoptosis in leukaemia cells. Nat Med 1996; 2(5):574-7.

Friesen C, Kiess Y, Debatin K M. A, critical role of glutathione in determining apoptosis sensitivity and resistance in leukaemia cells. Cell Death Differ 2004; 11(Suppl 1):S73-85.

Friesen C, Lubatschofski A, Kotzerke J, Buchmann I, Reske S N, Debatin K M. Beta-irradiation used for systemic radioimmunotherapy induces apoptosis and activates apoptosis pathways in leukaemia cells. Eur J Nucl Med 2003; 30:1251-61.

Hatsukari I, Hitosugi N, Matsumoto I, Nagasaka H, Sakagami H. Induction of early apoptosis marker by morphine in human lung and breast carcinoma cell lines. Anticancer Res. 2003 May-Jun; 23(3B):2413-7.

Hengartner M O. The biochemistry of apoptosis. Nature 2000; 407(6805):770-6.

Heusch W L, Maneckjee R. Effects of bombesin on methadone-induced apoptosis in lung cancer cells. Cancer Lett 1999; 136:177-85.

Kaufmann S H, Earnshaw W C. Induction of apoptosis by cancer therapy. Experimental Cell Research 2000; 256: 42-9.

Los M, Herr I, Friesen C, Fulda S, Schulze-Osthoff K, Debatin K-M. Cross-resistance of CD95- and drug-induced apoptosis as a consequence of deficient activation of caspases (ICE/Ced-3 proteases). Blood 1997; 90(8):3118-29.

Miles L, Raju U, Liao Z, Ajani J. Targeting molecular determinants of tumour chemo-radioresistance. Semin Oncol 2005; 32:78-81.

Nicoletti I, Migliorati G, Pagliacci M C, Grignani F, Riccardi C. A rapid and simple method for measuring thymocyte apoptosis by propidium iodide staining and flow cytometry. J Immunol Meth 1991;139:271-9.

Polakiewicz R D, Schieferl S M, Gingras A C, Sonenberg N, Comb M J. Mu-Opioid receptor activates signalling pathways implicated in cell survival and translational control. J Biol Chem. 1998 Sep 4; 273(36):23534-41.

DETAILED DESCRIPTION OF PREFERRED EMBODIMENTS

FIG. 1 indicates that the opioid methadone effectively induces apoptosis in leukaemia cells, but does not affect non-leucaemic, healthy PBL cells.

1A: CEM and HL-60 cells were treated with different concentrations of methadone as indicated. After 24 h (white bars) and 48 h (black bars) the percentages of apoptotic cells were measured by hypodiploid DNA analysis. The percentage of specific cell death was calculated as follows: 100× (experimental dead cells (%)—spontaneous dead cells in medium (%))/(100%—spontaneous dead cells in medium (%)). Data are given as mean of triplicates with a standard deviation (SD) of less than 10%. Similar results were obtained in three independent experiments.

1B: CEM and HL-60 cells (2×10$^5$ cells/mL) were treated with different concentrations of methadone as indicated or left untreated (Co, control). After 0h (white bars), 24 h (black bars) and 48 h (hatched bars) number of cells in 1 mL was counted. Data are given as mean of triplicates with a standard deviation (SD) of less than 10%. Similar results were obtained in three independent experiments.

1C: CEM cells (black bars) and PBLs (white bars) were treated with different concentrations of methadone as indicated. After 24 h and 48 h the percentages of apoptotic cells were measured by hypodiploid DNA analysis. The percentage of specific cell death was calculated as described in FIG. 1A. Data are given as mean of triplicates with a standard deviation (SD) of less than 10%. Similar results were obtained in three independent experiments.

FIG. 2 shows that the opioid methadone induces apoptosis in CD95-resistant (CEM$^{CD95R}$) and in doxorubicin-resistant (CEM$^{DoxoR}$) with comparable apoptosis rates to parental sensitive CEM leukaemia cells.

CEM (black bars), CEM$^{CD95R}$ (white bars) and CEM$^{DoxoR}$ (hatched bars) leukaemia cells were treated with different concentrations of methadone as indicated. After 24 h and 48 h the percentages of apoptotic cells was measured by the hypodiploid DNA analysis. The percentage of specific cell death was calculated as described in FIG. 1A. Data are given as mean of triplicates with a standard deviation (SD) of less than 10%. Similar results were obtained in three independent experiments.

Figure 3:
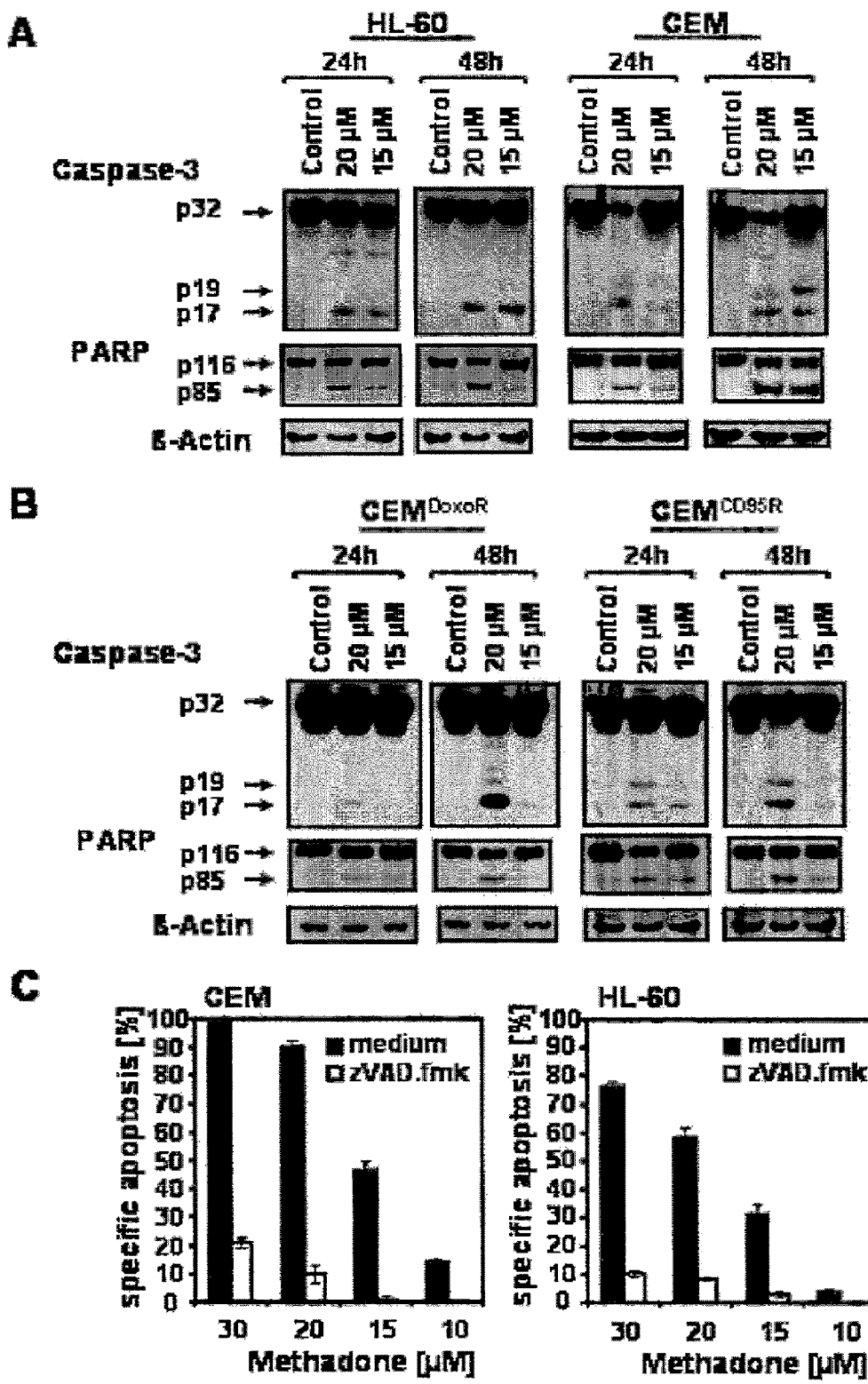

FIG. 3 shows that the opioid methadone induces caspases-dependent death in sensitive (HL-60, CEM), in doxorubicin-resistant (CEM$^{DoxoR}$) and in CD95-resistant (CEM$^{CD95R}$) leukaemia cells, which were multidrug-resistant and apoptosis-resistant.

3A: and 3B: Methadone induced activation of caspase-3 and PARP cleavage in HL-60, CEM, CEM$^{DoxoR}$ and CEM$^{CD95R}$ cells. A, HL-60, CEM, B, CEM$^{DoxoR}$ CEM$^{CD95R}$ cells were treated with different concentrations of methadone as indicated or left untreated (Control). After 24 h and 48 h Western blot analyses for caspase-3 and PARP were performed. The active fragment of caspase-3 was detected at ~19 and 17 kDa and the cleaved product of PARP at ~85 kDa. Equal protein loading was controlled by anti-beta-actin antibody.

3C: Inhibition of caspase activation with zVAD.fmk blocks methadone induced apoptosis in CEM and HL-60 cells. CEM and HL-60 cells were treated with different concentrations of methadone as indicated in the absence (black bars, medium) or presence (white bars, 50 µM zVAD.fmk) of 50 µM zVAD-.fmk. After 48 h the percentages of apoptotic cells were measured by hypodiploid DNA analysis. The percentage of specific cell death was calculated as described in FIG. 1A. Data are given as mean of triplicates with a standard deviation (SD) of less than 10%. Similar results were obtained in three independent experiments.

FIG. 4 shows that the opioid methadone activates the mitochondrial pathway in sensitive (HL-60, OEM), in doxorubicin-resistant (CEM$^{DoxoR}$) CD95-resistant (CEM$^{CD95R}$) leukaemia cells, which were multidrug-resistant and apoptosis-resistant.

4A and 4B: Methadone induced activation of caspase-9, down regulation of XIAP and down regulation of Bcl-x$_L$ in HL-60, CEM, CEM$^{DoxoR}$ and CEM$^{CD95R}$ cells.

HL-60, CEM (4A), $CEM^{DoxoR}$, CEM$^{CD95R}$ cells (4B) were treated with different concentrations of methadone as indicated or left untreated (Control). After 24 h and 48 h Western blot analyses for caspase-9, XIAP, and Bcl-x$_L$ were performed. The active fragment of caspase-9 was detected at ~37 kDa, XIAP was detected at ~58 kDa and Bcl-x$_L$ was detected at ~30 kDa. Equal protein loading was controlled by anti-beta-actin antibody.

FIG. 5 indicates that the opioid methadone induces apoptosis in glioblastoma cells.

A172 glioblastoma cells were treated with different concentrations of methadone as indicated. After 120 h (white columns), 144 h (black columns) and 168 h (hatched columns) the percentages of apoptotic cells were measured by hypodiploid DNA analysis.

The percentage of specific cell death was calculated as follows: 100×(experimental dead cells (%)—spontaneous dead cells in medium (%))/(100%—spontaneous dead cells in medium (%)). Data are given as mean of triplicates with a standard deviation (SD) of less than 10%. Similar results were obtained in three independent experiments.

FIG. 6 indicates that apoptosis can be successfully induced in glioblastoma cells by using combination of therapeutical concentrations of doxorubicin and low concentrations of methadone.

Glioblastom cells A172 (7000 cells/cm$^2$) were treated with a therapeutical concentration of 0.1 µg/mL doxorubicin (doxorubicin, white columns), with a low concentration of 1 µg/mL methadone (methadone, black columns), and with 0.1 µg/mL doxorubicin in addition of 1 µg/mL methadone (doxorubicin+methadone, hatched columns). After 72 h quantification of apoptosis was measured by flow cytometry. To determine apoptosis, cells were lysed with Nicoletti-buffer containing 0.1% sodium citrate plus 0.1% Triton X-100 and propidium iodide 50 µg/mL. Propidium iodide (PI) stained nuclei were analyzed by flow cytometry (FACSCalibur, Becton Dickinson, Heidelberg, Germany).

FIG. 7 indicates that apoptosis can be successfully induced in CEM cells, using the opioid cocaine.

CEM (white column) and HL-60 (black column) cells were treated with 1000 µg/mL of cocaine. After 48 h the percentages of apoptotic cells were measured by hypodiploid DNA analysis. The percentage of specific cell death was calculated as follows: 100×(experimental dead cells (%)—spontaneous dead cells in medium (%))/(100—spontaneous dead cells in medium (%)). Data are given as mean of triplicates with a standard deviation (SD) of less than 10%. Similar results were obtained in three independent experiments.

Figure 8:
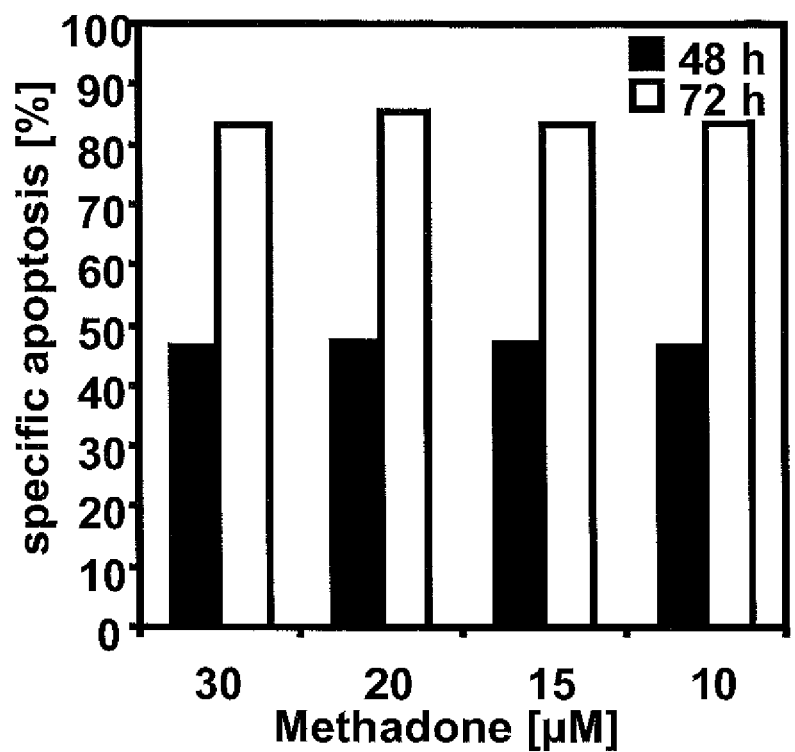

FIG. 8 indicates that D,L-methadone induces cell death in pre B-ALL (B-Cell lymphatic leukaemia) cells isolated from patients ex vivo.

B-ALL (B-Cell lymphatic leukaemia) cells (50000 cells/ 100 µl) were treated with 30, 20, 15, 10 pM methadone. After 48 h (black bars) and 72 h (white bars) quantification of apoptosis was measured by flow cytometry.

Figure 9:
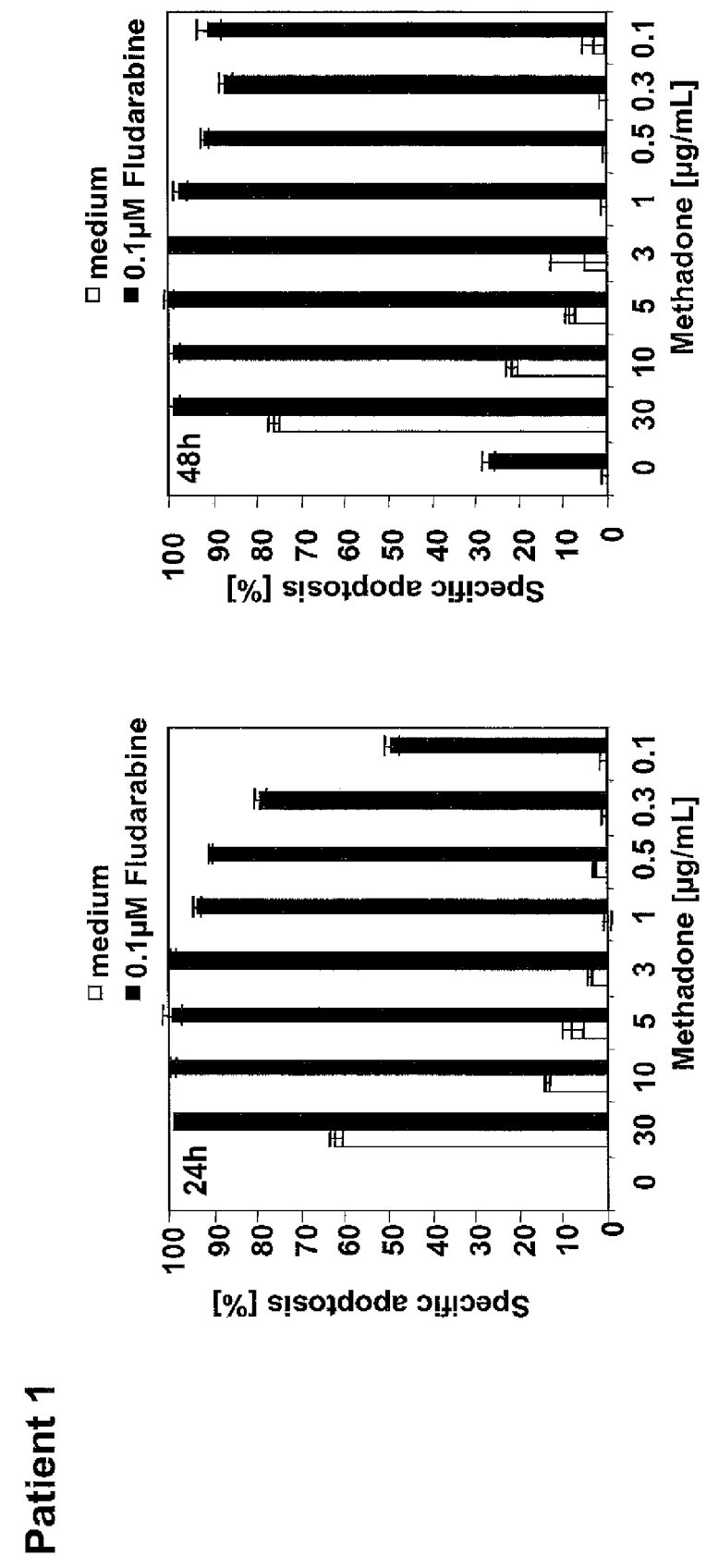

FIG. 9 indicates that D,L-methadone in combination with fludarabine induces cell death in resistant CLL (chronic lymphatic leukaemia) cells isolated from patients ex vivo.

CLL (chronic lymphatic leukaemia) cells (50000 cells/200 µl) were treated with 30, 10, 5, 3, 1, 0.5, 0.3, 0.1 µg/mL methadone alone (white bars) or in addition of 0.1 µM fludarabine (black bars). After 24 h and 48 h quantification of apoptosis was measured by flow cytometry.

Figure 10:
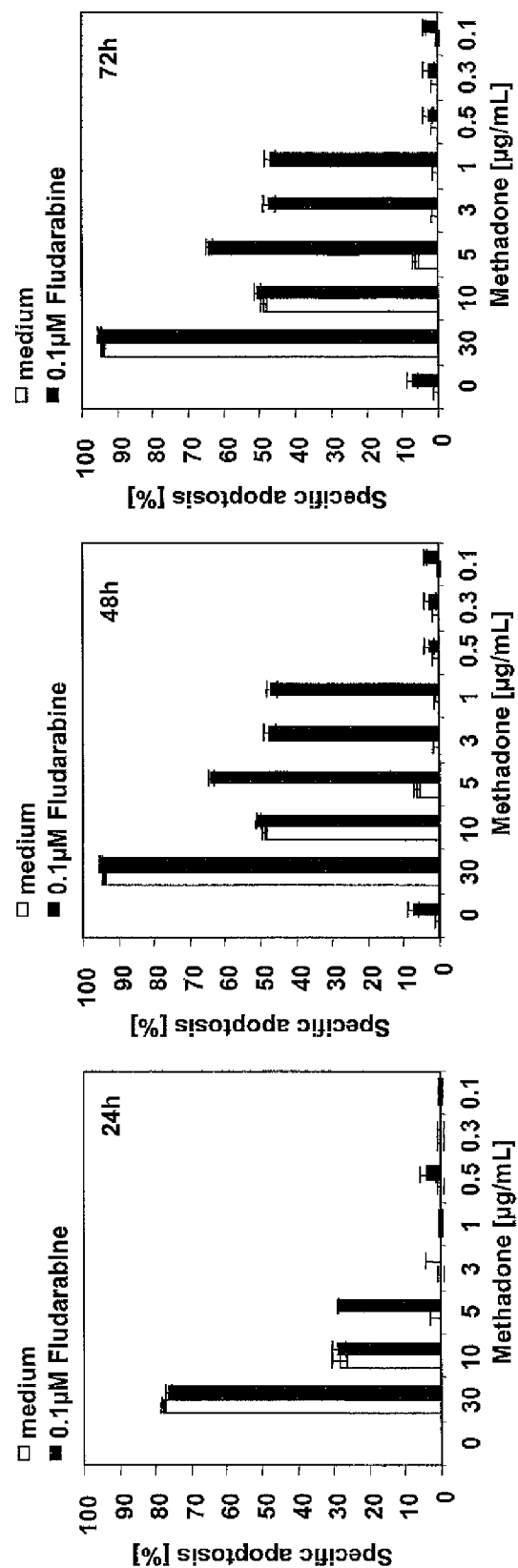

FIG. 10 indiCates that D,L-methadone in combination with fludarabine induces cell death in resistant CLL (chronic lymphatic leukaemia) cells isolated from patients ex vivo.

CLL (chronic lymphatic leukaemia) cells (50000 cells/200 µl) were treated with 30, 10, 5, 3, 1, 0.5, 0.3, 0.1 µg/mL methadone alone (white bars) or in addition of 0.1 µM fludarabine (black bars). After 24 h and 48 h quantification of apoptosis was measured by flow cytometry.

Figure 11:
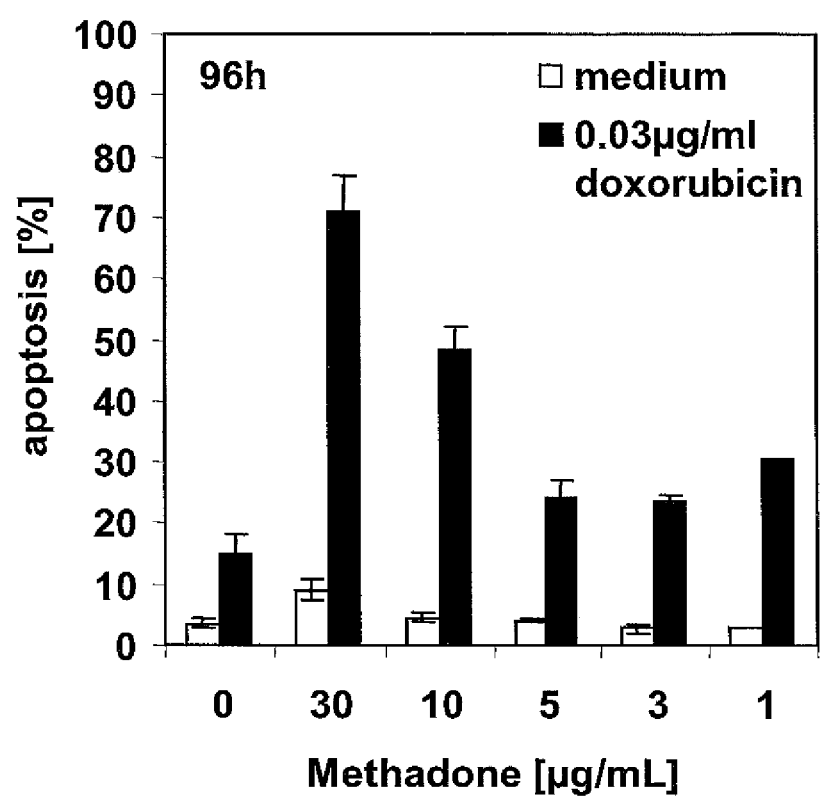

FIG. 11 shows the induction of apoptosis in the Human B cell leukaemia cell line Tanoue treated with doxorubicin+ methadone in vitro.

B-ALL (B-Cell lymphatic leukaemia) cell line Tanoue (5000 cells/100 µl) were treated with 30,10, 5, 3, 1 µg/mL methadone alone (white bars) or in addition of 0.03 µg/mL doxorubicin (black bars). After 96 h quantification of apoptosis was measured by flow cytometry.

Figure 12:
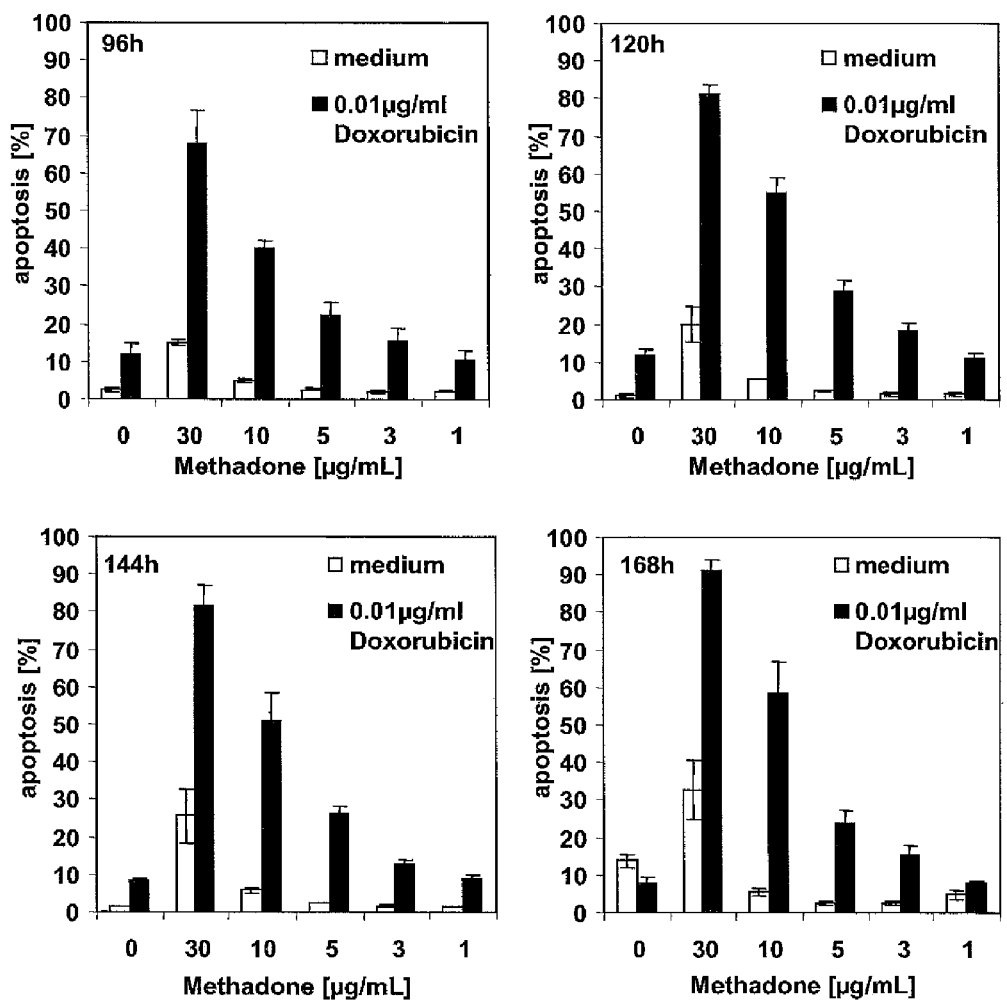

FIG. 12 shows the induction of apoptosis in the human B cell precursor leukaemia cell line Nalm6 treated with doxorubicin+methadone in vitro.

B-ALL (B-Cell lymphatic leukaemia) cell line Nalm6 (5000 cells/100 μl) were treated with 30,10, 5, 3, 1 μg/mL methadone alone (white bars) or in addition of 0.01 μg/mL doxorubicin (black bars). After 96 h, 120 h, 144 h, 168 h quantification of apoptosis was measured by flow cytometry.

Figure 13:
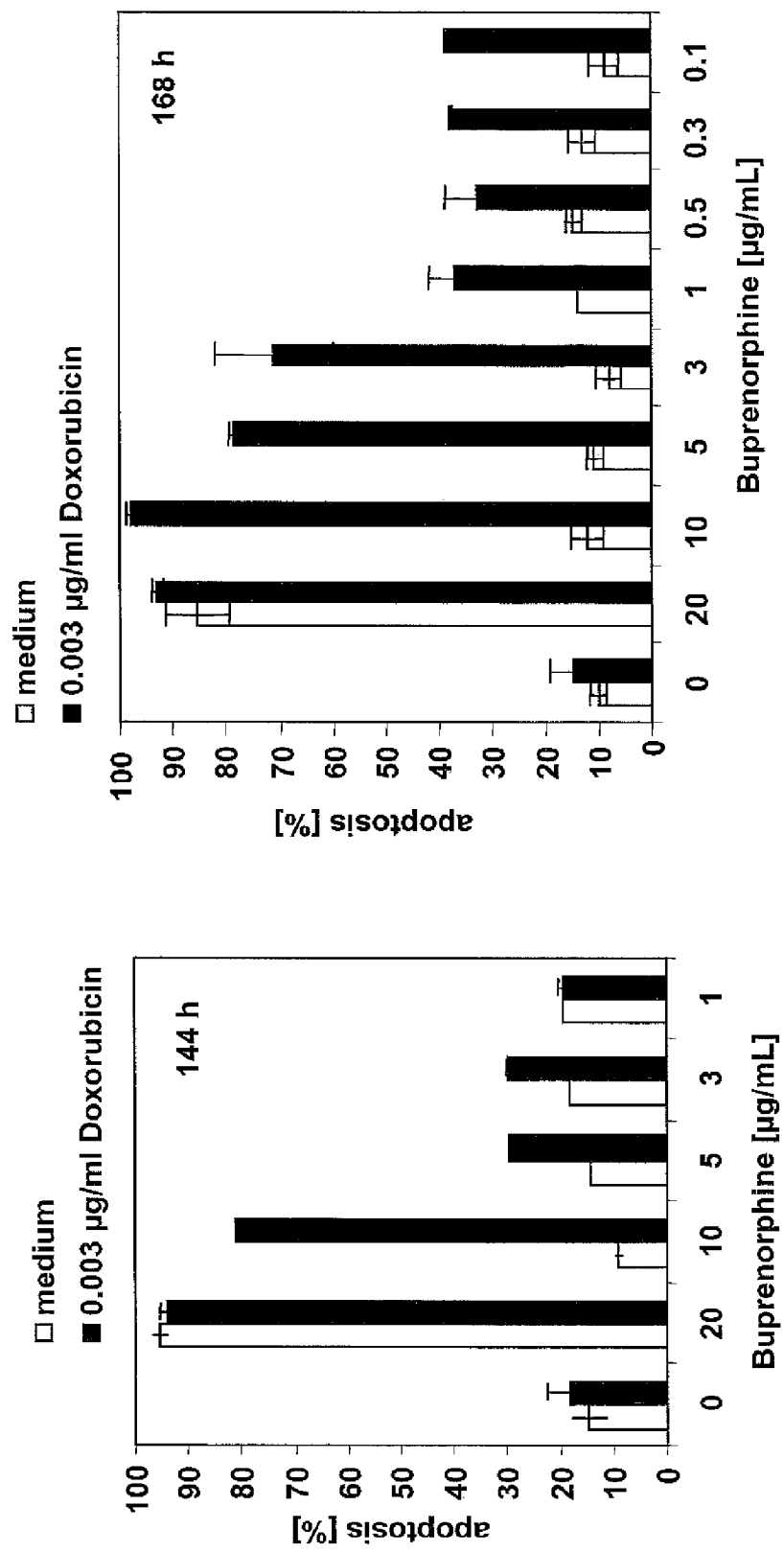

FIG. 13 shows the induction of apoptosis in the human acute myeloid leukaemia cell line HL-60 treated with doxorubicin+buprenorphine in vitro.

Human acute myeloid leukaemia HL-60 cell line (5000 cells/100 μl) were treated with 30,10, 5, 3, 1, 0.5, 0.3, 0.1 μg/mL buprenorphine alone (white bars) or in addition of 0.003μg/mL or 0.001 μg/mL doxorubicin (black bars). After 144 h or 168 h quantification of apoptosis was measured by flow cytometry.

FIG. 14 shows the induction of apoptosis in the human T cell leukaemia cell line CEM treated with doxorubicin+fentanyl in vitro.

Human T-Cell leukaemia CEM cell line (10000 cells/100 μl) were treated with 30,10, 5, 3,1, 0.5, 0.3, 0.1 μg/mL fentanyl alone (white bars) or in addition of 0.02 μg/mL doxorubicin (black bars). After 48 h and 72 h quantification of apoptosis was measured by flow cytometry.

Figure 15:
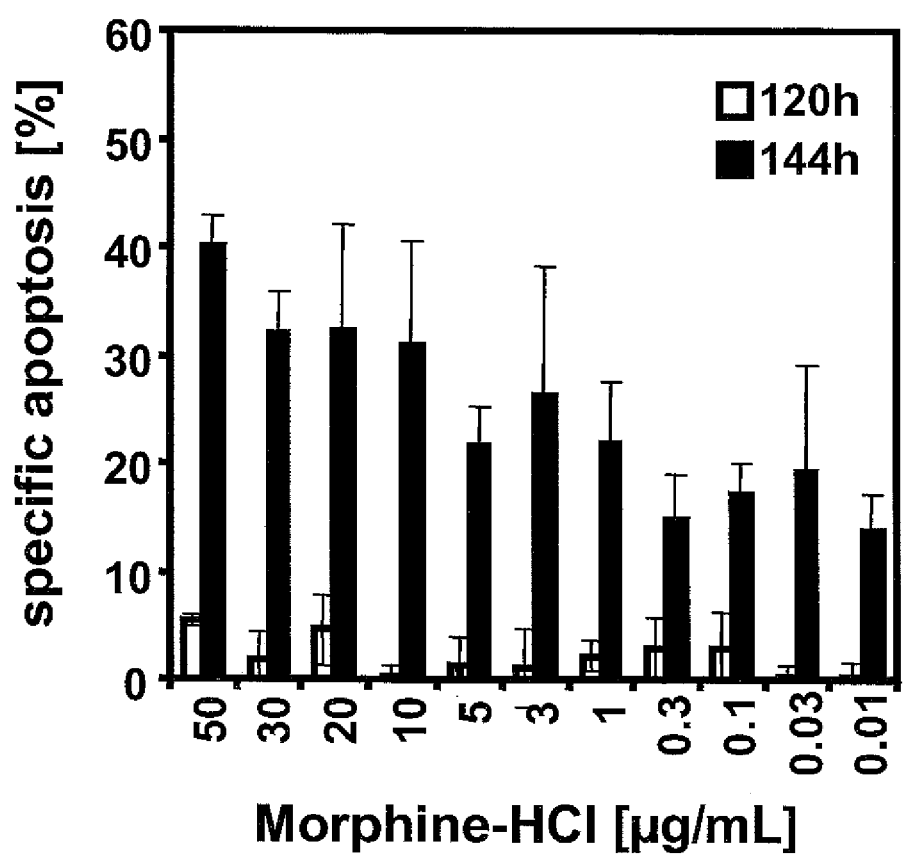

FIG. 15 shows the induction of apoptosis in the human acute myeloid leukaemia cell line HL-60 treated with morphine in vitro.

Human acute myeloid leukaemia HL-60 cell line (5000 cells/100 μl) were treated with 30,10, 5, 3, 1, 0.5, 0.3, 0.1, 0.03, 0.01 μg/mL morphine. After 120 h (white bars) or 144 h (black bars) quantification of apoptosis was measured by flow cytometry.

Figure 16:
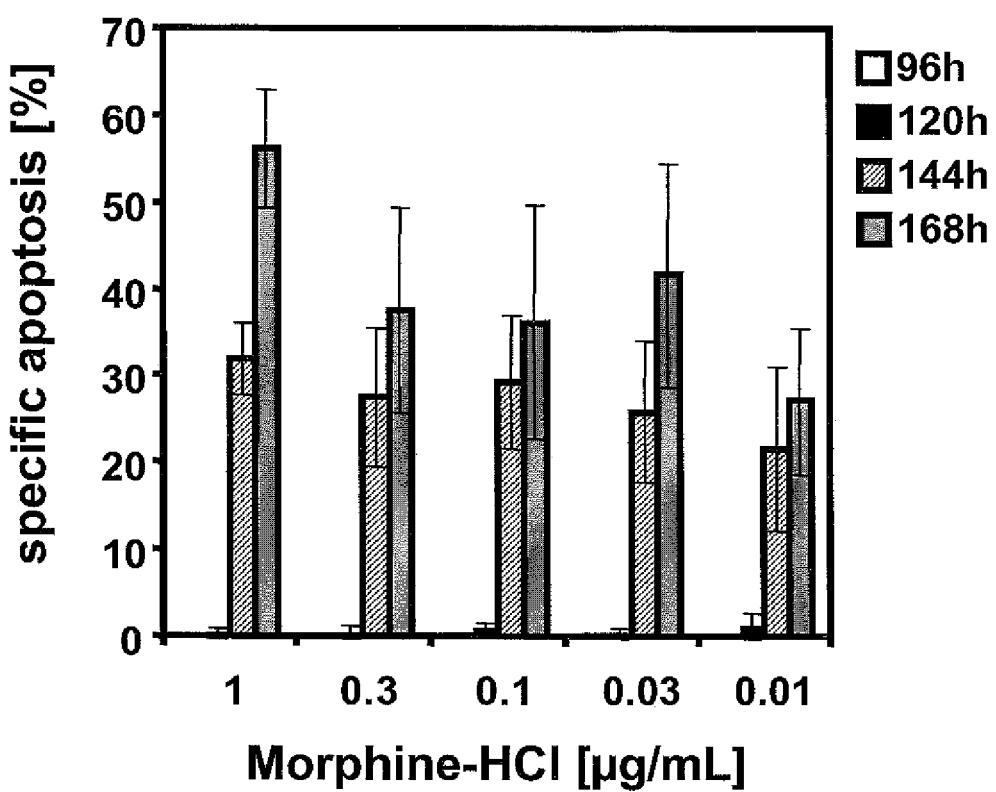

FIG. 16 shows the induction of apoptosis in the human acute myeloid leukaemia cell line HL-60 treated with morphine in vitro.

Human acute myeloid leukaemia HL-60 cell line (5000 cells/100 μl) were treated with 1, 0.5, 0.3, 0.1, 0.03, 0.01 μg/mL morphine. After 96 h (white bars), 120 h (black bars), 144 h (hatched bars) and 168 h (grey bars) quantification of apoptosis was measured by flow cytometry.

Figure 17:
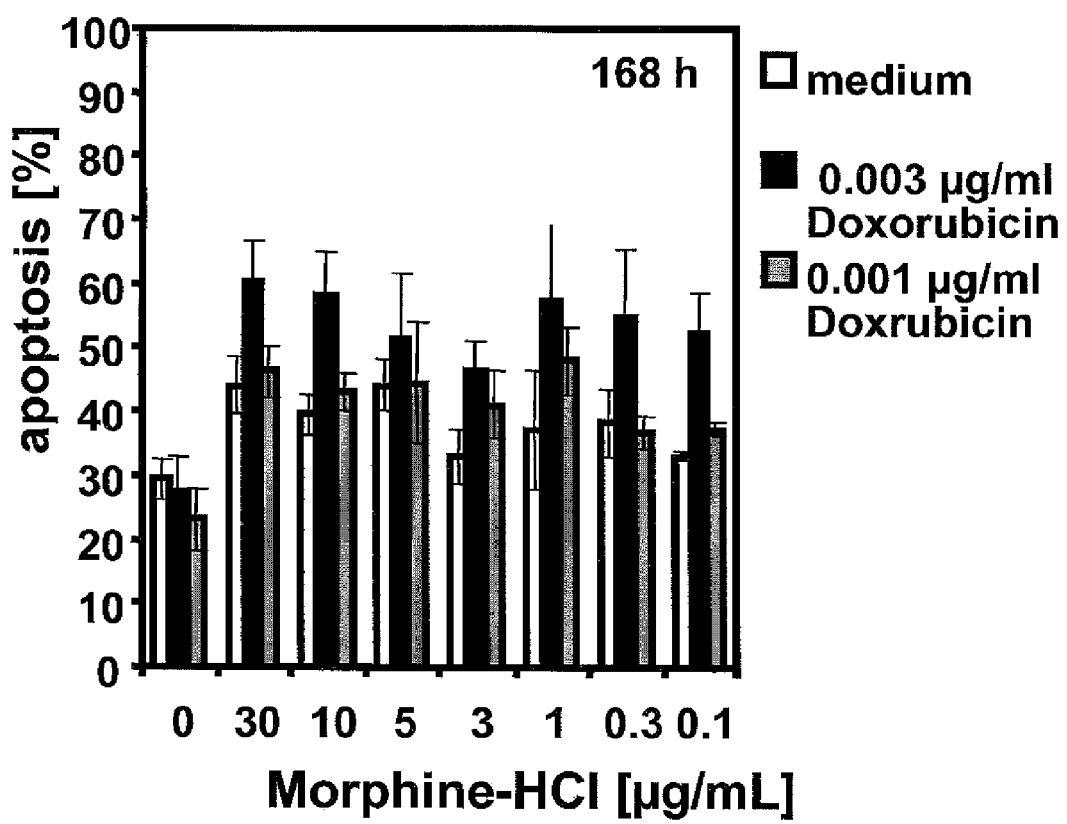

FIG. 17 shows the induction of apoptosis in the human acute myeloid leukaemia HL-60 treated with doxorubicin+ morphine in vitro.

Human acute myeloid leukaemia HL-60 cell line (5000 cells/100 μl) were treated with 30,10, 5, 3, 1, 0.5, 0.3, 0.1 μg/mL morphine alone (white bars) or in addition of 0.003 μg/mL (black bars) or 0.001 μg/mL doxorubicin (grey bars). After 168 h quantification of apoptosis was measured by flow cytometry.

What is claimed is:

1. A method of using opioids in treating resistant cancers in a patient comprising the step of:
administering to the patient with resistant cancer, a pharmaceutically effective amount of one or more opioids, wherein treating the resistant cancer occurs by inducing apoptosis through mitochondrial pathway in cancer cells thereby inhibiting cancer cell proliferation and/or inhibiting growth of cancer cells.

2. The method as claimed in claim 1, wherein the cancer patient exhibits at least one resistance from the group consisting of: apoptosis resistance, chemo resistance and radio resistance.

3. The method as claimed in claim 1, wherein the cancer patient exhibits either an intrinsic or an acquired resistance.

4. The method as claimed in claim 1, wherein the cancer patient exhibits one or more resistances of the group of resistances consisting of:
(i) apoptosis resistance
(ii) multi-drug resistance
(iii) anticancer drug resistance
(iv) cytotoxic drug resistance
(v) resistance to reactive oxygen species
(vi) resistance to DNA damaging agents
(vii) resistance to toxic antibodies
(viii) doxorubicin resistance
(ix) single or cross resistance, to one or more of drug substances selected from the group consisting of: methotrexate, cytarabine, cisplatine, etoposide, vincristine, paclitaxel (taxol), carboplatin, teniposide, dexamethasone, prednisolone, cyclophosphamide, iphosphamide, doxorubicin, epirubicin, daunorubicin, mercaptopurine, fludarabine, 5-fluoruracil,
(x) Irradiation resistance to alpha, beta, gamma or Auger electrons.

5. The method as claimed in claim 1, wherein the cancer patient suffers from one or more cancers consisting of: leukaemia, brain cancer, melanoma, pancreatic cancer, breast cancer, bladder cancer, colon carcinoma, liver cancer, ovarian cancer, cancer of mamma, lung cancer, chronic leukaemia or osteosarkoma.

6. The method of claim 1, wherein the treatment is for non-solid tumors selected from the group consisting of acute lymphoblastic leukaemia, B-cell lymphatic leukaemia, acute myeloid leukaemia, chronic myeloid leukaemia, chronic lymphocytic leukaemia, pro-forms of leukaemias, hairy cell leukaemia, Hodgkin's disease, Non-Hodgkin lymphoma and multiple myeloma.

7. The method of claim 1, wherein one or more of said opioids is capable of inducing apoptosis by at least one of the reactions from the group consisting of:
(xiii) cleavage of caspase-3 and PARP in the tumour cell
(xiv) cleavage of caspase-9 and down regulation of XIAP
(xv) down regulation of $Bcl_{XL}$.

8. The method of claim 1, wherein one or more of said opioids belongs to a methadone group.

9. The method of claim 8, wherein one of said opioids is a hydrochloride form of D-L-methadone.

10. The method of claim 1, wherein one or more of said opioids is selected from the group consisting of fentanyl, buprenorphine and morphine.

* * * * *